(12) United States Patent
Hirsch et al.

(10) Patent No.: US 7,070,810 B2
(45) Date of Patent: Jul. 4, 2006

(54) USE OF BUCKYSOME OR CARBON NANOTUBE FOR DRUG DELIVERY

(75) Inventors: Andreas Hirsch, Rathsberg (DE); Uri Sagman, Toronto (CA); Stephen R. Wilson, Houston, TX (US)

(73) Assignee: C Sixty Inc., Houston, TX (US)

(*) Notice: Subject to any disclaimer, the term of this patent is extended or adjusted under 35 U.S.C. 154(b) by 435 days.

(21) Appl. No.: 10/367,646

(22) Filed: Feb. 14, 2003

(65) Prior Publication Data

US 2003/0180491 A1    Sep. 25, 2003

Related U.S. Application Data

(60) Provisional application No. 60/356,856, filed on Feb. 14, 2002.

(51) Int. Cl.
*A61K 9/14* (2006.01)
*C01B 31/00* (2006.01)

(52) U.S. Cl. .............. 424/489; 977/DIG. 1; 423/445 B; 516/901

(58) Field of Classification Search ............... 424/489, 424/450; 560/80, 76, 8; 514/709; 423/445 B; 516/901; 977/DIG. 1
See application file for complete search history.

(56) References Cited

U.S. PATENT DOCUMENTS

| 5,466,587 A | 11/1995 | Fitzpatrick-McElligott et al. ............ 435/172.1 |
| 5,688,486 A * | 11/1997 | Watson et al. ............ 424/1.65 |
| 5,739,376 A | 4/1998 | Bingel ............ 560/51 |
| 5,811,460 A | 9/1998 | Friedman et al. ............ 514/563 |
| 6,204,391 B1 | 3/2001 | Friedman et al. ......... 548/338.1 |
| 6,397,102 B1 * | 5/2002 | Neuberger ............ 604/20 |
| 6,448,412 B1 * | 9/2002 | Murphy et al. ............ 548/417 |

FOREIGN PATENT DOCUMENTS

| WO | WO99/47570 | 9/1999 |
| WO | WO02/05803 | 1/2002 |

OTHER PUBLICATIONS

Mattson et al., "Molecular Functionalization of Carbon Nanotubes and Use as Substrates for Neuronal Growth," *Journal of Molecular Neuroscience* 14:175-182 (2000).
PCT/US03/04416 International Search Report (Sep. 22, 2001).
Braun et al., *Eur. J. Org. Chem.*, pp. 1173-1181 (2000).
Braun et al., *Carbon* 38:1565-1572 (2000).
Hirsch et al., *Eur. J. Org. Chem.*, pp. 829-848 (2001).
Brettreich et al., *Angew. Chem. Int. Ed.* 39:1845-1846 (2000).

* cited by examiner

*Primary Examiner*—Michael Hartley
(74) *Attorney, Agent, or Firm*—Williams, Morgan & Amerson, P.C.

(57) ABSTRACT

Compositions and methods for administering a therapeutic agent to a mammal are disclosed. The compositions comprise either (i) vesicles comprising an amphiphilic substituted fullerene, wherein the therapeutic agent is present in the vesicle interior or between layers of the vesicle wall, (ii) a substituted fullerene, comprising a fullerene core and a functional moiety, wherein the therapeutic agent is associated with the substituted fullerene, or (iii) carbon nanotubes, wherein the therapeutic agent is covalently bonded to the carbon nanotubes.

25 Claims, 8 Drawing Sheets

USE OF BUCKYSOME OR CARBON NANOTUBE FOR DRUG DELIVERY

This application claims priority from copending provisional application 60/356,856, filed Feb. 14, 2002, the disclosure of which is hereby incorporated by reference in its entirety.

BACKGROUND OF THE INVENTION

1. Field of the Invention

The present invention relates to compositions and methods for administering a therapeutic agent to a mammal. More particularly, it relates to vesicles, wherein the vesicle wall comprises substituted fullerenes and the vesicle comprises the therapeutic agent; derivatized carbon nanotubes, wherein the carbon nanotubes are derivatized with the therapeutic agent; and methods for administering the vesicles or derivatized carbon nanotubes to a mammal.

2. Description of Related Art

In recent years, a variety of approaches have been studied and used for drug delivery, DNA transfection, and other medical and biological applications. One such set of approaches involves vesicles or liposomes (the two terms will be used interchangeably herein).

Mishra et al., *Drug Deliv.* (2000) 7(3):155–159 teaches the loading of erythrocyte ghosts with doxorubicin HCl. So-called reverse biomembrane vesicles were formed by budding of membrane into the ghost interiors (endocytosis) leading to accumulation of small vesicles within each parent ghost. The amount of doxorubicin entrapped in reverse biomembrane vesicles was 0.75 mg/ml of packed vesicles. The in vitro release profile showed 52.86% of drug release in 16 hr.

Guo et al., *Drug Deliv.* (2000) 7(2):113–116 teaches the preparation of flexible lecithin vesicles containing insulin and assessed the effect of these vesicles on the transdermal delivery of insulin. When vesicles were applied onto mice abdominal skin, blood glucose dropped by greater than 50% within 18 hr.

Freund, Drug Deliv. (2001) 8(4):239–244 teaches the encapsulation of therapeutic molecules in a noncationic multilamellar vector comprising phosphatidylcholine, cholesterol, and polyoxyethylene alcohol. Such vectors with entrapped drugs were prepared by shearing a phospholipidic lyotropic lamellar phase.

However, a need remains in the art for vesicles which possess properties suitable for drug delivery, namely low toxicity of the amphiphiles from which the vesicles are formed and ready vesicle formation and disaggregation, among others. Such properties are also of interest regarding non-vesicle-based drug delivery systems, as well.

Fullerenes, of which the best known example is $C_{60}$, were first reported by Kroto et al., *Nature* (1985) 318:162. Since then, the ready derivatization of fullerenes has allowed a wide variety of derivatized fullerenes to be prepared and their properties explored.

Amphiphilic derivatized fullerenes have been reported by Hirsch et al., *Angew. Chem. Int. Ed.* (2000) 39(10):1845–1848. The derivatized fullerenes of Hirsch comprised one dendrimeric group comprising 18 carboxylic acid moieties and five hydrophobic moieties each comprising a pair of lipophilic $C_{12}$ hydrocarbon chains. Freeze-fracture electron micrography of aqueous solutions of the amphiphilic derivatized fullerenes revealed that the amphiphilic derivatized fullerenes formed bilayer vesicles (by which is meant, a vesicle defined by a membrane comprising an external layer of amphiphilic derivatized fullerene molecules substantially all oriented with their hydrophilic groups to the exterior of the vesicle, and an internal layer of amphiphilic derivatized fullerene molecules substantially all oriented with their hydrophilic groups to the interior of the vesicle, wherein the hydrophobic groups of the molecules of the external layer are in close proximity to the hydrophobic groups of the molecules of the internal layer) with diameters from about 100 nm to about 400 nm.

Braun et al., *Eur. J. Org. Chem.* (2000) 1173–1181, teaches the synthesis of biotinated lipofullerenes.

Carbon nanotubes and methods for their derivatization are known. Holzinger et al., *Angew. Chem. Int. Ed.* (2001) 40(21):4002–4005 report the cycloaddition of nitrenes, the addition of nucleophilic carbenes, and the addition of radicals, to the sidewalls of carbon nanotubes.

SUMMARY OF THE INVENTION

In one embodiment, the present invention relates to a vesicle having an interior, an exterior, and a wall, wherein the wall comprises one or more layers, wherein each layer comprises a substituted fullerene having structure I:

$$(B)_b\text{—}C_n\text{-}(A)_a \qquad (I)$$

wherein $C_n$ is a fullerene moiety comprising n carbon atoms, wherein n is an integer and $60 \leq n \leq 240$;

B is an organic moiety comprising from 1 to about 40 polar headgroup moieties;

b is an integer and $1 \leq b \leq 5$;

each B is covalently bonded to the $C_n$ through 1 or 2 carbon-carbon, carbon-oxygen, or carbon-nitrogen bonds;

A is an organic moiety comprising a terminus proximal to the $C_n$ and one or more termini distal to the $C_n$, wherein the termini distal to the $C_n$ each comprise —$C_xH_y$, wherein x is an integer and $8 \leq x \leq 24$, and y is an integer and $1 \leq y \leq 2x+1$;

a is an integer, $1 \leq a \leq 5$;

$2 \leq b+a \leq 6$; and each A is covalently bonded to the $C_n$ through 1 or 2 carbon-carbon, carbon-oxygen, or carbon-nitrogen bonds, wherein the vesicle wall comprises at least about 50 mol % the substituted fullerene, and the interior of the vesicle, a portion of the wall between two layers, or both comprise a therapeutic agent.

In another embodiment, the present invention relates to a method of administering a therapeutic agent to a mammal, comprising:

(i) administering a solution comprising a pharmaceutically effective amount of the therapeutic agent, wherein the therapeutic agent is present in the interior of a vesicle, a portion of the vesicle wall between two layers, or both to the mammal, wherein the vesicle is as defined above.

In yet another embodiment, the present invention relates to a method of reversibly forming a vesicle comprising a therapeutic agent in the interior thereof, between two layers of the wall thereof, or both, comprising:

dissolving in an aqueous solvent a substituted fullerene having the structure I, as described above, and the therapeutic agent, wherein the pH of the solvent is sufficiently low to form a vesicle from the substituted fullerene.

In still another embodiment, the present invention relates to a derivatized carbon nanotube, comprising:

a carbon nanotube, and at least one therapeutic agent, wherein each therapeutic agent is covalently attached to the carbon nanotube.

In yet a further embodiment, the present invention relates to a method of delivering a therapeutic agent to a tissue of a mammal, comprising (i) administering to the mammal a derivatized carbon nanotube, comprising a carbon nanotube and at least one therapeutic agent, wherein each therapeutic agent is covalently attached to the carbon nanotube, and (ii) administering to the mammal an adjuvant which promotes disruption of the covalent bond between the carbon nanotube and the at least one therapeutic agent when the derivatized carbon nanotube is in proximity to the tissue, thereby delivering the at least one therapeutic agent to the tissue.

The present invention allows for the convenient preparation of compositions that can readily deliver a therapeutic agent to a specific tissue. The ability to target the therapeutic agent to a specific tissue allows the use of smaller doses of the therapeutic agent and may reduce systemic side effects of the therapeutic agent. Further, the substituted fullerenes and the carbon nanotubes used in the various embodiments of the present invention are readily cleared from the body after delivering the therapeutic agent.

DESCRIPTION OF ILLUSTRATIVE EMBODIMENTS

Figure 1:
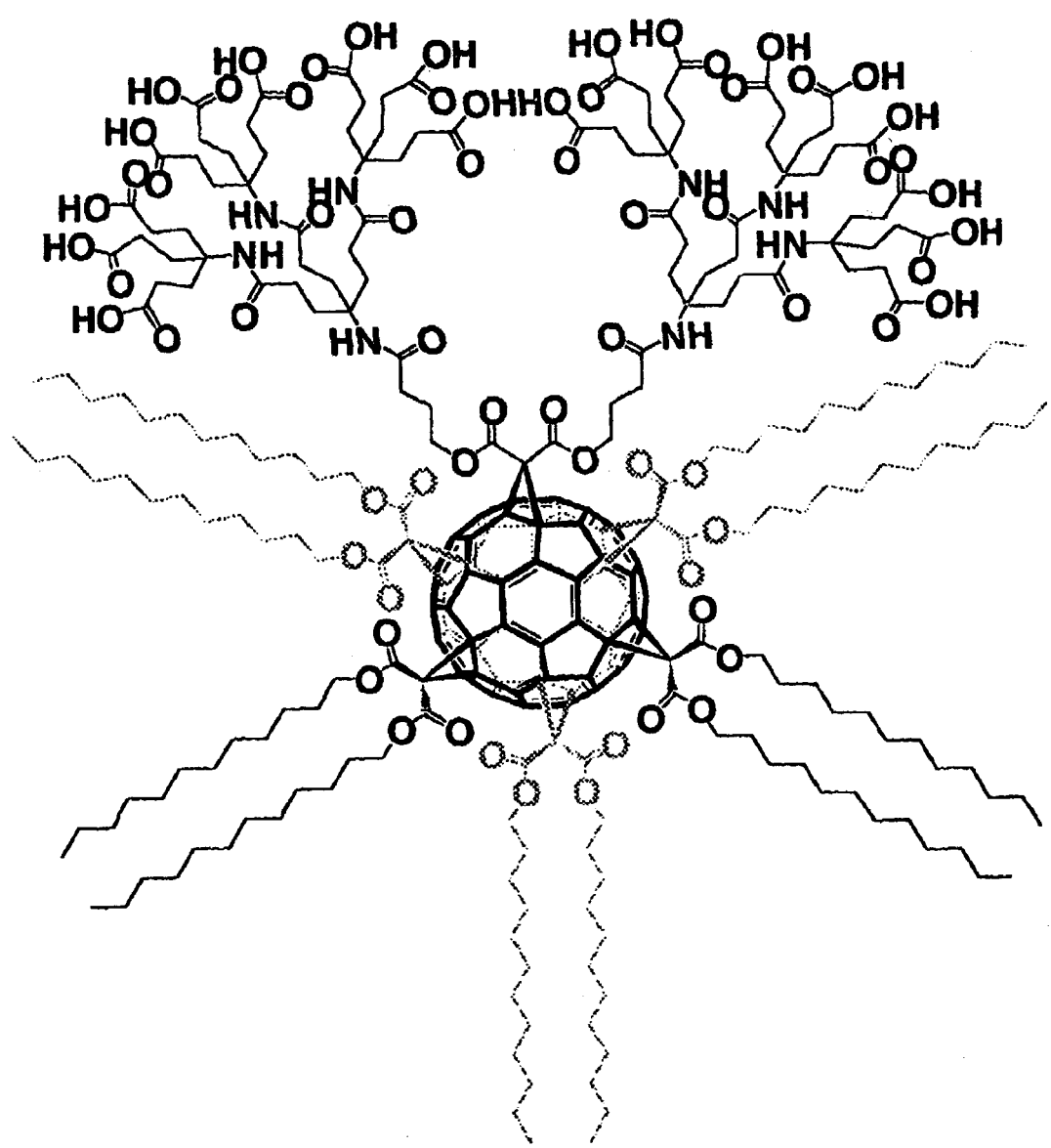
FIG. 1 shows a particular substituted fullerene (which may be referred to as an "amphifullerene") of the present invention. The use of gray to represent three >C(C(=O)O(CH$_2$)$_{11}$CH$_3$)$_2$ moieties indicates these three moieties are bonded to the fullerene core at regions of the fullerene which are not directly visible to the putative observer in this orientation.

In one embodiment, the present invention relates to a vesicle having an interior, an exterior, and a wall, wherein the wall comprises one or more layers, wherein each layer comprises a substituted fullerene having structure I:

(B)$_b$—C$_n$-(A)$_a$   (I)

wherein C$_n$ is a fullerene moiety comprising n carbon atoms, wherein n is an integer and 60≦n≦240;

B is an organic moiety comprising from 1 to about 40 polar headgroup moieties;

b is an integer and 1≦b≦5;

each B is covalently bonded to the C$_n$ through 1 or 2 carbon-carbon, carbon-oxygen, or carbon-nitrogen bonds;

A is an organic moiety comprising a terminus proximal to the C$_n$ and one or more termini distal to the C$_n$, wherein the termini distal to the C$_n$ each comprise —C$_x$H$_y$, wherein x is an integer and 8≦x≦24, and y is an integer and 1≦y≦2x+1;

a is an integer, 1≦a≦5;

2≦b+a≦6; and each A is covalently bonded to the C$_n$ through 1 or 2 carbon-carbon, carbon-oxygen, or carbon-nitrogen bonds, wherein the vesicle wall comprises at least about 50 mol % the substituted fullerene, and wherein the interior of the vesicle, a portion of the wall between two layers, or both comprise a therapeutic agent.

A "vesicle," as the term is used herein, is a collection of amphiphilic molecules, by which is meant, molecules which include both (a) hydrophilic ("water-loving") regions, typically charged or polar moieties, such as moieties comprising polar headgroups, among others known to one of ordinary skill in the art, and (b) hydrophobic ("water-hating") regions, typically apolar moieties, such as hydrocarbon chains, among others known to one of ordinary skill in the art. In aqueous solution, the vesicle is formed when the amphiphilic molecules form a wall, i.e., a closed three-dimensional surface. The wall defines an interior of the vesicle and an exterior of the vesicle. Typically, the exterior surface of the wall is formed by amphiphilic molecules oriented such that their hydrophilic regions are in contact with water, the solvent in the aqueous solution. The interior surface of the wall may be formed by amphiphilic molecules oriented such that their hydrophilic regions are in contact with water present in the interior of the vesicle, or the interior surface of the wall may be formed by amphiphilic molecules oriented such that their hydrophobic regions are in contact with hydrophobic materials present in the interior of the vesicle.

The amphiphilic molecules in the wall will tend to form layers, and therefore, the wall may comprise one or more layers of amphiphilic molecules. If the wall consists of one layer, it may be referred to as a "unilayer membrane" or "monolayer membrane." If the wall consists of two layers, it may be referred to as a "bilayer membrane." Walls with more than two layers, up to any number of layers, are also within the scope of the present invention.

The vesicle may be referred to herein as a "buckysome."

"C$_n$" refers to a fullerene moiety comprising n carbon atoms. Buckminsterfullerenes, also known as fullerenes or, more colloquially, buckyballs, are cage-like molecules consisting essentially of sp$^2$-hybridized carbons. Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. Common fullerenes include C$_{60}$ and $C_{70}$, although fullerenes comprising up to about 400 carbon atoms are also known. Herein,

is used as a representation of a $C_{60}$ molecule or a $C_{60}$ moiety in a molecule.

Fullerenes can be produced by any known technique, including, but not limited to, high temperature vaporization of graphite. Fullerenes are or are expected to be commercially available from MER Corporation (Tucson, Ariz.) and Frontier Carbon Corporation, among other sources.

The naming of specific substituted $C_{60}$ isomers is complex. Within the present specification, the so-called Hirsch Scheme (Hirsch, *Angew. Chem. Intl. Ed.* (1994) 33(4): 437–438) will be used.

Methods of substituting fullerenes with various substituents are well known in the art. Methods include 1,3-dipolar additions (Sijbesma et al., *J. Am. Chem. Soc.* (1993) 115: 6510–6512; Suzuki, *J. Am. Chem. Soc.* (1992) 114:7301–7302; Suzuki et al., *Science* (1991) 254:1186–1188; Prato et al., *J. Org. Chem.* (1993) 58:5578–5580; Vasella et al., *Angew. Chem. Int. Ed. Engl.* (1992) 31:1388–1390; Prato et al., *J. Am. Chem. Soc.* (1993) 115:1148–1150; Maggini et al., *Tetrahedron Lett.* (1994) 35:2985–2988; Maggini et al., *J. Am. Chem. Soc.* (1993) 115:9798–9799; and Meier et al., *J. Am. Chem. Soc.* (1994) 116:7044–7048), Diels-Alder reactions (Iyoda et al., *J. Chem. Soc. Chem. Commun.* (1994) 1929–1930; Belik et al., *Angew. Chem. Int. Ed. Engl.* (1993) 32:78–80; Bidell et al., *J. Chem. Soc. Chem. Commun.* (1994) 1641–1642; and Meidine et al., *J. Chem. Soc. Chem. Commun.* (1993) 1342–1344), other cycloaddition processes (Saunders et al., *Tetrahedron Lett.* (1994) 35:3869–3872; Tadeshita et al., *J. Chem. Soc. Perkin. Trans.* (1994) 1433–1437; Beer et al., *Angew. Chem. Int. Ed. Engl.* (1994) 33:1087–1088; Kusukawa et al., *Organometallics* (1994) 13:4186–4188; Averdung et al., *Chem. Ber.* (1994) 127:787–789; Akasaka et al., *J. Am. Chem. Soc.* (1994) 116:2627–2628; Wu et al., *Tetrahedron Lett.* (1994) 35:919–922; and Wilson, *J. Org. Chem.* (1993) 58:6548–6549); cyclopropanation by addition/elimination (Hirsch et al., *Agnew. Chem. Int. Ed. Engl.* (1994) 33:437–438 and Bestmann et al., *C. Tetra. Lett.* (1994) 35:9017–9020); and addition of carbanions/alkyl lithiums/Grignard reagents (Nagashima et al., *J. Org. Chem.* (1994) 59:1246–1248; Fagan et al., *J. Am. Chem. Soc.* (1994) 114:9697–9699; Hirsch et al., *Agnew. Chem. Int. Ed. Engl.* (1992) 31:766–768; and Komatsu et al., *J. Org. Chem.* (1994) 59:6101–6102); among others.

The synthesis of substituted fullerenes is reviewed by Murphy et al., U.S. Pat. No. 6,162,926.

It has been found that fullerenes, especially $C_{60}$, readily receive up to six adducts in an octahedral addition pattern (an octahedron having six vertices) (Brettreich et al., *Angew. Chem. Int. Ed.* (2000) 39:1845–1848).

B is chosen from any organic moiety comprising from 1 to about 40 polar headgroup moieties. A "polar headgroup" is a moiety which is polar, by which is meant that the vector sum of the bond dipoles of each bond within the moiety is nonzero. A polar headgroup can be positively charged, negatively charged, or neutral. The polar headgroup can be located such that at least a portion of the moiety can be exposed to the environment of the molecule. Exemplary polar headgroup moieties can include, but are not limited to, carboxylic acid, alcohol, amide, and amine moieties, among others known in the art. Preferably, B has from about 6 to about 24 polar headgroup moieties. In one embodiment, B has a structure wherein the majority of the polar headgroup moieties are carboxylic acid moieties, which are exposed to water when the substituted fullerene is dissolved in an aqueous solvent. A dendrimeric or other regular highly-branched structure is suitable for the structure of B.

The value of b can be any integer from 1 to 5. In one embodiment, if more than one B group is present (i.e., b>1), that all such B groups are adjacent to each other. By "adjacent" in this context is meant that no B group has only A groups, as defined below, and/or no substituent groups at all the nearest neighboring points of addition. In the case of an octahedral addition pattern when b>1, "adjacent" means that the four vertices of the octahedron in closest proximity to the B group are not all A groups or null.

In one embodiment, B comprises 18 polar headgroup moieties and b=1.

The polar headgroup moieties of B tend to make the B group or groups hydrophilic.

Each B is bonded to $C_n$ through a covalent bond or bonds. Any covalent bond which a fullerene carbon is capable of forming and will not disrupt the fullerene structure is contemplated. Examples include carbon-carbon, carbon-oxygen, or carbon-nitrogen bonds. One or more atoms, such as one or two atoms, of the B group can participate in bonding to $C_n$. In one embodiment, one carbon atom of the B group is bonded to two carbon atoms of $C_n$, wherein the two carbon atoms of $C_n$ are bonded to each other.

In one embodiment, B has the amide dendron structure

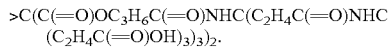

In structure I, A is an organic moiety comprising a terminus proximal to the $C_n$ and one or more termini distal to the $C_n$. In one embodiment, the organic moiety comprises two termini distal to $C_n$. By "terminus proximal to $C_n$" is meant a portion of the A group that comprises one or more atoms, such as one or two atoms, of the A group which form a bond or bonds to $C_n$. By "terminus distal to $C_n$" is meant a portion of the A group that does not comprise any atoms which form a bond or bonds to $C_n$, but that does comprise one or more atoms which form a bond or bonds to the terminus of the A group proximal to $C_n$.

Each terminus distal to the $C_n$ comprises —$C_xH_y$, wherein x is an integer and $8 \leq x \leq 24$, and y is an integer and $1 \leq y \leq 2x+1$. The —$C_xH_y$ can be linear, branched, cyclic, aromatic, or some combination thereof. Preferably, A comprises two termini distal to $C_n$, wherein each —$C_xH_y$ is linear, $12 \leq x \leq 18$, and y=2x+1. More preferably, in each of the two termini, x=12 and y=25.

The termini distal to $C_n$ tend to make the A groups hydrophobic or lipophilic.

The value of a can be any integer from 1 to 5. Preferably, a is 5. In one embodiment, if more than one A group is present (i.e., a>1), all such A groups are adjacent to each other. By "adjacent" in this context is meant that no A group has only B groups, as defined below, and/or no substituent groups at all the nearest neighboring points of addition. In the case of an octahedral addition pattern, when a>1, "adjacent" means that the four vertices of the octahedron in closest proximity to the A group are not all B groups or null.

Each A is bonded to $C_n$ through a covalent bond or bonds. Any covalent bond which a fullerene carbon is capable of forming and will not disrupt the fullerene structure is contemplated. Examples include carbon-carbon, carbon-oxygen, or carbon-nitrogen bonds. One or more atoms, such as one or two atoms, of the A group can participate in bonding to $C_n$. In one embodiment, one carbon atom of the A group is bonded to two carbon atoms of $C_n$, wherein the two carbon atoms of $C_n$ are bonded to each other.

In one embodiment, A has the structure $>C(C(=O)O(CH_2)_{11}CH_3)_2$.

The number of B and A groups is chosen to be from 2 to 6, i.e., $2 \leq b+a \leq 6$. In one embodiment, b+a=6. The combination of hydrophilic B group(s) and hydrophobic A group(s) renders the substituted fullerene amphiphilic. The number and identity of B groups and A groups can be chosen to produce a fullerene with particular amphiphilic qualities which may be desirable for particular intended uses.

In one preferred embodiment, the substituted fullerene has structure II:

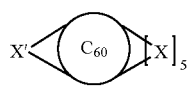

(II)

wherein X' is $>C(C(=O)OC_3 H_6 C(=O)NHC(C_2 H_4 C(=O)NHC(C_2H_4C(=O)OH)_3)_3)_2$ and each X is $>C(C(=O)O(CH_2)_{11}CH_3)_2$. A structural representation of a substituted fullerene having structure II is given in FIG. 1, wherein each X is $>C(C(=O)O(CH_2)_{11}CH_3)_2$.

In one embodiment, the substituted fullerene has the structure shown in FIG. 1.

The substituted fullerene can further comprise one or more functional groups covalently linked to one or more B groups, one or more A groups, or both. In one embodiment, the one or more functional groups are covalently linked to one or more B groups.

By "functional group" is meant a group that binds to a specific compound, and thus allows the substituted fullerene to be associated with the specific compound.

In one embodiment, the functional group is biotin or a biotin-containing moiety, i.e., a moiety which will bind to streptavidin.

In another embodiment, the functional group is an antigen-binding moiety, by which is meant a moiety comprising the antigen-recognition site of an antibody. Examples of a moiety comprising the antigen-recognition site of an antibody include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, among others. Single chain or multiple chain antigen-recognition sites can be used. Multiple chain antigen-recognition sites can be fused or unfused.

The antigen-binding moiety can be selected from any known class of antibodies. Known classes of antibodies include, but are not necessarily limited to, IgG, IgM, IgA, IgD, and IgE. The various classes also can have subclasses. For example, known subclasses of the IgG class include, but are not necessarily limited to, IgG1, IgG2, IgG3, and IgG4. Other classes have subclasses that are routinely known by one of ordinary skill in the art.

The antigen-binding moiety can be selected from an antibody derived from any species. "Derived from," in this context, can mean either prepared and extracted in vivo from an individual member of a species, or prepared by known biotechnological techniques from a nucleic acid molecule encoding, in whole or part, an antibody peptide comprising invariant regions which are substantially identical to antibodies prepared in vivo from an individual member of the species or an antibody peptide recognized by antisera specifically raised against antibodies from the species. Exemplary species include, but are not limited to, human, chimpanzee, baboon, other primate, mouse, rat, goat, sheep, and rabbit, among others known in the art. In one embodiment, the antibody is chimeric, i.e., comprises a plurality of portions, wherein each portion is derived from a different species. A chimeric antibody, wherein one of the portions is derived from human, can be considered a humanized antibody.

Antigen-recognition moieties are available that recognize antigens associated with a wide variety of cell types, tissues, and organs, and a wide variety of medical conditions, in a wide variety of mammalian species. Exemplary medical conditions include, but are not limited to, cancers, such as lung cancer, oral cancer, skin cancer, stomach cancer, colon cancer, nervous system cancer, leukemia, breast cancer, cervical cancer, prostate cancer, and testicular cancer; arthritis; infections, such as bacterial, viral, fungal, or other microbial infections; and disorders of the skin, the eye, the vascular system, or other cell types, tissues, or organs; among others.

Exemplary antigen-recognition moieties known in the art include, but are not limited to, those derived from antibodies against vascular endothelial growth factor receptor (VEGF-r) (available from Imclone, New York, N.Y.), antibodies against epidermal growth factor receptor (EGF-r) (available from Abgenix, Fremont, Calif.), antibodies against polypeptides associated with lung cancers (available from Corixa Corporation, Seattle, Wash.), antibodies against human tumor necrosis factor alpha (hTNF-α) (available from BASF A.G., Ludwigshafen, Germany), among others known in the art.

Antigen-recognition moieties can be prepared by various techniques known in the art. These techniques include, but are not limited to, the immunological technique described by Kohler and Milstein in Nature 256, 495–497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA techniques described by Huse et al in Science 246, 1275–1281 (1989); among other techniques known to one of ordinary skill in the art.

In a further embodiment, the functional group is a tissue-recognition moiety, by which is meant a moiety that recognizes cells of a particular tissue by binding specifically with one or more proteins expressed by cells of the tissue and present on the exterior of the cells. Examples of such moieties include, but are not limited to, peptides, among other classes of moieties. The term "peptides," as used herein, encompasses any peptide comprising 1 or more amino acids. Exemplary peptides include, but are not limited to, VEGF, EGF, other growth factors, and other ligands for receptors (such as cell surface receptors, cytoplasmic receptors, and nuclear receptors), among others.

In one embodiment, wherein the polar headgroups are carboxylic acid moieties and the functional group is a peptide, a functional group can be linked to a polar headgroup via an amino linkage between a carboxylic acid in the polar headgroup and an amine in the peptide.

Tissue-recognition moieties can be derived from any species or plurality of species, and can be selected to target any cell type, tissue, or organ, or treat any disease.

The inclusion of functional groups will enhance targeting of a substituted fullerene to a particular tissue. The inclusion of functional groups in at least some of the substituted fullerene molecules of the vesicle membrane will enhance the targeting of the vesicle to a particular tissue.

The functional group can also comprise a linker or linkers, i.e., moieties which are covalently bonded to both (a) the biotin-containing moiety, the antigen-binding moiety, or the tissue-recognition moiety, as defined above, and (b) the substituted fullerene, as defined above. In one embodiment, wherein the polar headgroups are carboxylic acid moieties, the linker can be an ester.

If some of the substituted fullerene molecules in the vesicle membrane comprise a functional group, from about 0.01 mole % to about 100 mole % of the substituted fullerene molecules of the vesicle membrane comprise the functional group. In the interest of reduced expense, and in light of the observation that many functional groups are highly sensitive to the specific compounds which they bind, preferably from about 0.01 mole % to about 1 mole % of the substituted fullerene molecules of the vesicle membrane comprise the functional group.

In one embodiment, the vesicle wall comprises at least about 50 mol % of the substituted fullerene. The balance of the vesicle membrane comprises other amphiphilic compounds. By "amphiphilic compound" in this context is meant a compound whose molecules each comprise hydrophobic and hydrophilic regions. Such amphiphilic compounds include, but are not limited to, commercially-available lipids, such as dimethyl dioctadecyl ammonium bromide, phosphatidylcholine, and dioleoyltrimethylammonium phosphate, among others.

In one embodiment, the vesicle wall comprises at least about 75 mol % a substituted fullerene having structure I. In another embodiment, the vesicle wall consists essentially of a substituted fullerene having structure I.

In one embodiment, the vesicle wall is a bilayer membrane. The bilayer membrane comprises two layers, an interior layer formed from substituted fullerene and other amphiphilic compound or compounds, if any, wherein substantially all substituted fullerene and other amphiphilic molecules are oriented with their hydrophobic portions toward the exterior layer, and an exterior layer formed from substituted fullerene and other amphiphilic compound or compounds, if any, wherein substantially all substituted fullerene and other amphiphilic molecules are oriented with their hydrophobic portions toward the interior layer. As a result, the hydrophilic portions of substantially all molecules of each of the interior and exterior layers are oriented towards aqueous solvent in the vesicle interior or exterior to the vesicle.

Because the hydrophilicity of the hydrophilic portions of the molecules may change if the pH or other parameters of the solvent are changed (e.g., if the pH is increased above the pKa of the polar headgroup moieties of the B groups of the substituted fullerenes, the substituted fullerenes will readily separate from the vesicle membrane and enter the aqueous phase), the pH and other parameters of the solvent can be adjusted as a matter of routine experimentation by one of ordinary skill in the art in order to allow vesicle formation.

Because the vesicle comprises an interior, and the interior comprises an aqueous solvent, the vesicle can further comprise a therapeutic agent in the interior of the vesicle. Typically, such a compound is introduced to the interior of the vesicle as part of the process of forming the vesicle, e.g., by introducing the therapeutic agent, the substituted fullerene, and other amphiphilic compounds, if any, into an aqueous solvent under pH and other conditions whereby the substituted fullerene and other amphiphilic compounds, if any, self-assemble a vesicle, with molecules of the therapeutic agent being sequestered in the vesicle during vesicle self-assembly. To facilitate self-assembly, preferably the pH of the solvent is less than about 8.0. However, other techniques of including a therapeutic agent in the interior of the vesicle known in the art can be used.

In one embodiment, when the interior of the vesicle comprises water and substantially does not comprise a hydrophobic solvent, the therapeutic agent is a water-soluble drug or other compound which, upon administration to a mammal, can alleviate a medical condition from which the mammal suffers. In one embodiment, the therapeutic agent is selected from the group consisting of water-soluble anti-cancer drugs.

In one embodiment, the vesicle wall is a monolayer membrane, in which molecules of the substituted fullerene and other amphiphilic compound(s), if any, are substantially all oriented such that their hydrophilic regions are adjacent to a polar or aqueous phase, either in the vesicle interior or exterior to the vesicle, and their hydrophobic regions are adjacent to an apolar phase, either in the vesicle interior or exterior to the vesicle. In this context, "polar" and "apolar" are relative terms, in that a phase with greater hydrophilicity, miscibility with water, etc. is more polar than a phase with poorer solubility in water. In one embodiment, in the vesicle the hydrophobic regions of substantially all the molecules of the monolayer membrane are oriented toward the interior of the vesicle.

In one embodiment, when the interior of the vesicle comprises a hydrophobic solvent or other apolar material and substantially does not comprise water, the therapeutic agent is a hydrophobic drug or other compound which, upon administration to a mammal, can alleviate a medical condition from which the mammal suffers. The terms "hydrophobic" and "lipophilic" are synonyms wheresoever they appear herein.

Any hydrophobic compound can be included in the vesicle interior, typically by providing the substituted fullerene, other amphiphilic compounds, if any, and the hydrophobic compound in an aqueous solvent under pH and other conditions wherein a monolayer membrane will form, and allowing the vesicle to self-assemble, during which process the hydrophobic compound will be sequestered in the interior of the vesicle. To facilitate assembly of the vesicle, preferably the pH of the solvent is less than about 8.0.

The vesicle can be unilamellar (having a single bimolecular membrane), multilamellar (having a plurality of bimolecular membranes, "onion-like") or hemilamellar (having a single unimolecular membrane). The vesicle can have a size from about 50 Angstroms to about 10 microns. The size, number and nature of membranes, and other parameters of the vesicle can be adjusted as a matter of routine experimentation.

In one embodiment, the therapeutic agent is associated with a fullerene, such as a substituted fullerene comprising a functional group, among others. The association can be a covalent link between the fullerene core and the therapeutic agent; a covalent link between a substituent of the fullerene, if any, and the therapeutic agent; an ionic association between a positively- or negatively-charged group on the substituent of the fullerene and an oppositely-charged group on the therapeutic agent; or the encapsulation of the therapeutic agent in the fullerene core, among others. A covalent link can be direct or it can make use of a covalent linker linking the therapeutic agent and the fullerene core or substituent, if any, of the fullerene. In one embodiment, the covalent link can be cleaved by an appropriate cleaving technique, such as photolysis, enzymatic cleavage, or chemical cleavage, among others. In another embodiment, a non-covalent association between the therapeutic agent and the fullerene can be dissociated by application of an appropriate chemical, e.g., when the association is an ionic association, the association can be dissociated by application of a charged compound of the same charge as the charged group on the therapeutic agent. Other techniques for dissociating a non-covalent association between the substituted fullerene and the therapeutic agent will be apparent to one of ordinary skill in the art in light of the present specification. A chemical or enzyme used to promote dissociation can be referred to as an "adjuvant."

Any therapeutic agent, from any source, can be used. As is known in the art, therapeutic agents can be invented by rational drug design, combinatorial chemistry, or serendipitous discovery, among other known techniques. Naturally occurring therapeutic agents can be derived from a plant, an animal, a bacterium, a fungus, a virus, or another organism. Therapeutic agents can be synthesized by known chemical synthesis techniques.

The therapeutic agent can treat any disease. Exemplary diseases include, but are not limited to, cancers, autoimmune diseases, infections, liver diseases, and neurological diseases, among many others.

In one embodiment, the therapeutic agent is an anti-cancer drug. Examples of anti-cancer drugs include paclitaxel (commercially available as Taxol, Bristol-Myers Squibb), doxorubicin (also known under the trade name Adriamycin), vincristine (known under the trade names Oncovin, Vincasar PES, and Vincrex), actinomycin D, altretamine, asparaginase, bleomycin, busulphan, capecitabine, carboplatin, carmustine, chlorambucil, cisplatin, cyclophosphamide, cytarabine, dacarbazine, daunorubicin, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, UFT (uracil-tegufur), vinblastine, and vindesine, among others.

Other therapeutic agents include, but are not limited to, the following: hydrocodone, atorvastatin, estrogen, atenolol, levothyroxine, azithromycin, furosemide, amoxicillin, amlodipine, alprazolam, albuterol, loratadine, hydrochlorothiazide, omeprazole, sertraline, paroxetine, triamterene, lansoprazole, ibuprofen, celecoxib, simvastatin, cephalexin, metformin, rofecoxib, lisinopril, amoxicillin, clavulanate, propoxyphene, progesterone, prednisone, norgestimate, ethinyl estradiol, acetaminophen, codeine, cetirizine, fexofenadine, levothyroxine, amoxicillin, metoprolol, lorazepam, metoprolol, fluoxetine, ranitidine, zolpidem, citalopram, amitriptyline, alendronate, quinapril, sildenafil citrate, pravastatin, naproxen, gabapentin, warfarin, ciprofloxacin, verapamil, digoxin, albuterol, bupropion, lisinopril, clonazepam, tramadol, cyclobenzaprine, trazodone, fluticasone, montelukast, diazepam, isosorbide mononitrate s.a., glyburide, venlafaxine, levofloxacin, medroxyprogesterone, amoxicillin, fluconazole, enalapril, warfarin, carisoprodol, trimeth, sulfameth, fluticasone propionate, benazepril, mometasone, doxycycline, estradiol, allopurinol, rosiglitazone maleate, clopidogrel, propranolol, amlodipine, benazepril, methylprednisolone, valsartan, losartan, insulin, clonidine, diltiazem, loratidine, pseudoephedrine, latanoprost, pioglitazone, loratidine, pseudoephedrine, risperidone, fexofenadine, pseudoephedrine, doxazosin, raloxifene, norethindrone, folic acid, penicillin, oxycodone, temazepam, diltiazem, salmeterol, fosinopril, oxycodone, ramipril, promethazine, terazosin, olanzapine, gemfibrozil, levothyroxine, norethindrone, sumatriptan, hydroxyzine, meclizine, losartan, rabeprazole, phenytoin, clarithromycin, glimepiride, pantoprazole, spironolactone, ipratropium, albuterol, tamsulosin, penicillin, lisinopril, metoclopramide, minocycline, bisoprolol, digoxin, valsartan, metronidazole, cefprozil, triamcinolone, glipizide, norethindrone, levonorgestrel, cefuroxime, nystatin, captopril, promethazine, codeine, acyclovir, norgestimate, oxycodone, irbesartan, nefazodone, mirtazapine, valacyclovir, methylphenidate, cerivastatin, fluoxetine, nitrofurantoin, loratadine, glyburide, metformin, metformin, diltiazem, desogestrel, mupirocin, 1-norgestrel, fluvastatin, aspirin, clarithromycin, clindamycin, esomeprazole, metaxalone, nortriptyline, cimetidine, fenofibrate, iprotropium bromide, tamoxifen, calcitonin salmon, felodipine, levonorgestrel, salmeterol, fluticasone, theophylline, tetracycline, tolterodine, gatifloxacin, nifedipine, diclofenac, triamcinolone acetonide, promethazine, indomethacin, benzonatate, phenobarbital, naproxen sodium, mometasone, hydrocodone, glipizide, divalproex, nitroglycerin, and phenazopyridine, among others.

One or more therapeutic agents can be used in any composition or method of the present invention.

The mode of action of the therapeutic agent can be chemotherapeutic, radiotherapeutic, or possess another mode of action. In one embodiment, the therapeutic agent can mediate the application of light, heat, or other external energy in a manner which allows the light, heat, or other external energy to perform a therapeutic action.

In one embodiment, the therapeutic agent is present between two layers of the wall. The therapeutic agent, in this embodiment, may be a water-soluble compound or a lipophilic compound.

In another embodiment, the vesicle can comprise a sensor molecule. A "sensor molecule," as used herein, is a molecule which can selectively associate with a particular atom or molecule. Any sensor molecule known in the art can be used. The sensor molecule can be linked with a fullerene or anchored in the vesicle wall by hydrophobic, hydrophilic, or both types of interactions.

In a further embodiment, the vesicle can comprise a diagnostic agent. A "diagnostic agent," as used herein, is a molecule which can be readily detected by the application of electromagnetic radiation, heat, cooling, the measurement of radioactivity, or other techniques known in the art. The diagnostic agent can be linked with a fullerene or anchored in the vesicle wall by hydrophobic, hydrophilic, or both types of interactions.

In another embodiment, the present invention relates to a method of administering a therapeutic agent to a mammal, comprising:

(i) administering a solution comprising a pharmaceutically effective amount of the therapeutic agent, wherein the therapeutic agent is present in (a) the interior of a vesicle having an interior, an exterior, and a wall, (b) a portion of the wall between two layers, or (c) both, to the mammal, wherein the wall comprises one or more layers and each layer comprises a substituted fullerene having structure I.

The vesicle, the substituted fullerene, and the therapeutic agent are as described above. In one embodiment, the vesicle wall comprises at least about 75 mol % a substituted fullerene having structure I. In another embodiment, the vesicle wall consists essentially of a substituted fullerene having structure I.

In one embodiment, the vesicle wall is a monolayer membrane. In another embodiment, the vesicle wall is a bilayer membrane.

In one embodiment, from about 0.01 mole % to about 100 mole % of the substituted fullerene molecules in the vesicle wall further comprise a functional group covalently linked to a B group and the functional group recognizes a tissue. In another embodiment, the functional group is selected from the group consisting of biotin-containing moieties, antigen-binding moieties, and tissue-recognition moieties, as defined above.

The pharmaceutically effective amount of the therapeutic agent will vary depending on the compound, the intended effect thereof, the administration regimen, and the body weight or other characteristics of the mammal, among others apparent to one of ordinary skill in the art. The dose of the therapeutic agent will typically be in the range of from about 0.001 mg/kg body weight to about 1000 mg/kg body weight. In one embodiment, the dose of the therapeutic agent will typically be within the above range and greater than about 0.01 mg/kg body weight. In another embodiment, the dose of the therapeutic agent will typically be within the above range and less than about 100 mg/kg body weight.

In one embodiment, the therapeutic agent is an anti-cancer drug. More preferably, the anti-cancer drug is selected from the group consisting of paclitaxel, doxorubicin, and vincristine.

Any technique for incorporating the therapeutic agent in the vesicle interior or between layers of the vesicle wall can be used. An exemplary technique is described above, wherein the vesicle is formed in the presence of the therapeutic agent in an aqueous solvent under pH and other conditions wherein the vesicle can form. This technique can be performed on either a batch or a continuous basis. Other techniques, however, can be used, such as microinjection of a solution of the therapeutic agent into the vesicle interior, among others.

In the administering step, a solution comprising the vesicle and the therapeutic agent in the interior thereof, between two layers of the wall thereof, or both is introduced into the mammal. The solution comprises a polar or aqueous solvent and the vesicle comprising the therapeutic agent. The solution can further comprise adjuvants, preservatives, and other compounds whose inclusion in light of the formation, storage, and/or use of the solution may be desirable.

Any mammal for which it is desired to introduce the therapeutic agent can be the subject of the method. In one embodiment, the mammal is a human.

The term "administering," as used herein, is intended to encompass all techniques of introducing a compound to a mammal. Exemplary routes of administration include transdermal, subcutaneous, intravenous, intraarterial, intramuscular, oral, rectal, and nasal, among others.

In one embodiment, the vesicle comprises substituted fullerenes further comprising a functional group with identity and concentration as described above. A vesicle comprising such substituted fullerenes can be directed toward a particular tissue.

"Particular tissue" in this context is not meant to be limiting to one cell type, but may be meant to refer to specific bodily fluids, specific organs comprising a variety of tissues, etc. Particular tissues to which it may be desirable to direct the vesicles include, but are not limited to, gastrointestinal tissues, circulatory tissues, lymphatic tissues, biliary tissues, cerebrospinal fluid, synovial fluid, the aqueous humor of the eye, and tumors in the foregoing or any other tissue or cell type.

Fullerenes themselves generally have toxicological properties similar to those of carbon, and substituted fullerenes are generally not expected to possess toxic activities. For example, repeated transdermal administration of fullerenes in benzene for up to 24 weeks (dose=200 µg/day) to mice did not result in either benign or malignant skin tumor formation (Nelson et al., *Toxicology & Indus. Health* (1993) 9(4): 623–630). Further, no effect on either DNA synthesis or ornithine decarboxylase activity in dermal cells was observed over a 72-hr time course after treatment. Zakharenko et al., *Doklady Akademii Nauk.* (1994) 335(2): 261–262, have shown that $C_{60}$ did not produce chromosomal damage at relatively high doses.

In one embodiment, the functional group interacts directly with the particular tissue. For example, if the functional group is an antigen-binding moiety, and the antigen recognized by the moiety is a protein present on the surface of cells of a particular tissue, then the is functional group will bind the protein and direct the vesicle to the particular tissue. In another example, if the functional group is a tissue-recognition moiety, then the functional group will recognize a particular tissue and direct the vesicle to the particular tissue. Antigen-binding and tissue-recognition moieties, and the antigens they bind and tissues they recognize, are well known in the art. Other direct interactions between the functional group and a particular tissue are possible and are contemplated as part of the present invention.

In another embodiment, the functional group interacts indirectly with a particular tissue. By this is meant that the functional group interacts with an adjuvant, and the adjuvant interacts with a particular tissue. "Adjuvant" as used herein refers to any molecule, whether occurring in vivo or introduced by administration to the mammal, which provides a beneficial function. In one embodiment, the adjuvant comprises an antigen-binding moiety or a tissue-recognition moiety and a streptavidin moiety, and the functional group of the substituted fullerene comprises a biotin-containing moiety. The vesicle interacts with the adjuvant through the biotin-containing moiety of the substituted fullerene and the streptavidin moiety of the adjuvant, and the adjuvant interacts with a particular tissue through the antigen-binding moiety or tissue-recognition moiety as described above.

Adjuvants can provide other or additional beneficial functions. In one embodiment, an adjuvant facilitates union of the vesicle with the membrane of a cell of a tissue. The union of the vesicle with the membrane will lead to introduction of the therapeutic agent contained within the vesicle into the cytoplasm of the cell.

Many useful adjuvants are not present in vivo in the mammal. Therefore, in one embodiment, the method further comprises administering an adjuvant to the mammal, wherein the adjuvant facilitates recognition of the tissue by a functional group, union of the vesicle with the membrane of a cell of the tissue, or both. The adjuvant is as described above, and can be administered via any route of administration, as described above. The adjuvant can be administered before, after, or simultaneously with the solution comprising the vesicle. Typically, the adjuvant is administered via the same route as the solution comprising the vesicle, but the adjuvant can be administered by a different route, if desired.

In one embodiment, the method allows the systemic distribution of the therapeutic agent to the mammal, through in vivo disaggregation of the vesicle. The method allows the direction of the vesicle comprising the therapeutic agent to a particular tissue. In many cases, it is desirable to release the therapeutic agent when the vesicle is in close proximity to the particular tissue.

One technique by which the therapeutic agent can be released in close proximity to the tissue involves union of the vesicle with the membrane of a cell of the tissue. Union can be facilitated by use of particular adjuvants, as described above.

Another set of techniques by which the therapeutic agent can be released in close proximity to the tissue involves disaggregation of the vesicle when the vesicle is in close proximity to the tissue. One such technique involves raising the pH of bodily fluids in which the vesicle is present. By raising the pH of such bodily fluids, the number of charged carboxyl groups (—COO⁻) on the B group of the substituted fullerene will increase and, depending on the pH and the precise structure of the substituted fullerene, molecules of the substituted fullerene may find it more favorable in free energy terms to enter the aqueous solution than to remain in the vesicle membrane. This leads to disaggregation of the vesicle and release of the therapeutic agent. Therefore, in one embodiment, the method further comprises raising the pH of bodily fluids in which the solution comprising the vesicle and the therapeutic agent in the interior thereof is present to a pH at which the vesicle disaggregates. In one embodiment, the pH is raised to greater than about 11.0.

Any technique appropriate for raising the pH can be used. Typically, raising the pH can be performed by administering a solution to the mammal comprising a compound that will raise the pH of bodily fluids, e.g., a basic solution. Such a solution can be administered via any route described above or known in the art.

Another technique for disaggregating the vesicle lies in the observation that some substituted fullerenes, such as some substituted fullerenes formed from Diels-Alder cycloaddition reactions, readily lose their substituent groups at temperatures slightly above room temperature depending on the diene structure of the substituent, and that some other substituted fullerenes, such as aldehyde-derived adducts, readily lose their substituent groups under moisture or heat. The B groups, A groups, or both of the substituted fullerene can be chosen to be added to the fullerene through such reactions. As a result, depending on the nature of the substituent groups and other parameters apparent to one of ordinary skill in the art, and as a matter of routine experimentation, the substituted fullerene can be designed such that it loses B groups, A groups, or both upon or soon after administration. The loss of B groups, A groups, or both would reduce the amphiphilic character of the substituted fullerene, and as a result, would reduce its ability to form or maintain the vesicle membrane. This would be expected to disaggregate the vesicle.

A further technique for disaggregation of the vesicle is natural disaggregation when the vesicle is in contact with a bodily fluid. This process may be accelerated by the presence of factors (proteins, lipids, salts, etc.) which may be present in the bodily fluid. This process may occur without further intervention by the operator of the method.

Another technique for disaggregation of the vesicle involves the use of photocleavable polar headgroups. Photocleavable moieties, such as —Ar(NO$_2$)CH$_2$—, wherein Ar is an aromatic moiety, can be used to link the fullerene core with the polar headgroups, and vesicles can be formed from such substituted fullerenes. Upon irradiation of the vesicle of this embodiment by electromagnetic radiation of an appropriate wavelength, the photocleavable moiety can be cleaved and the resulting removal of polar headgroups from the substituted fullerene can lead to disaggregation of the vesicle.

A further technique for disaggregation of the vesicle involves the use of ultrasonic energy. Upon exposing a region of a mammalian body to sufficient ultrasonic energy, vesicles present in the region can disaggregate and release a therapeutic agent, if any, associated with the vesicle. The vesicles could be present in the region as a result of targeting to a specific cell type, tissue, or organ, or could be present in the region as a result of systemic circulation.

Another technique for disaggregation of the vesicle involves the use of biological sensor molecules associated with the vesicle, such as sensor moieties covalently linked with a fullerene molecule in the vesicle wall or sensor molecules anchored by hydrophobic, hydrophilic, or both types of interactions with the vesicle wall. A particular sensor molecule can detect atoms and molecules present in bodily fluids, such as blood. Exemplary atoms and molecules present in blood include glucose; minerals, such as calcium, potassium, or sodium, among others; hormones, such as insulin, thyroid hormone, testosterone, estrogen, or growth factors, among others; peptides; enzymes; or blood constituents, such as red blood cell surface molecules, white blood cell surface molecules, platelets, or extracellular hemoglobin, among others; among others. In one embodiment, the sensor molecule can be chosen such that, upon encountering a bodily region wherein the bodily fluid has an excess of the atom or molecule detectable by the sensor molecule, the sensor molecule binds the atom or molecule and leaves the vesicle or the sensor molecule undergoes a conformational change. In either case, if the sensor molecule, the vesicle, and other features are properly chosen, the vesicle can disaggregate. Alternatively, the sensor molecule can be chosen such that disaggregation of the vesicle occurs upon encountering a bodily region wherein the bodily fluid has a shortage of the atom or molecule.

In one embodiment, the present invention relates to a method of diagnosing a medical condition in a mammal, comprising:

(i) administering a solution comprising a pharmaceutically effective amount of a diagnostic agent, wherein the diagnostic agent is present in (a) the interior of a vesicle having an interior, an exterior, and a wall, (b) a portion of the wall between two layers, or (c) both, wherein the vesicle is as described above and comprises fullerenes substituted with a functional group, as described above, to the mammal; and (ii) detecting the diagnostic agent.

Any agent which is detectable by any means can be the "diagnostic agent." In one embodiment, the diagnostic agent is a fluorophore, which can be made to fluoresce upon exposure to a particular wavelength of electromagnetic radiation. In another embodiment, the diagnostic agent is a radionuclide, which can be detected by known techniques. Other diagnostic agents are known in the art.

The method is similar to the method of treatment described above, except that instead of releasing a therapeutic agent to a particular cell type or tissue, a diagnostic agent is directed to the vicinity of the cell type or tissue by the use of a vesicle comprising fullerenes substituted with functional groups such as antigen-binding moieties or tissue-recognition moieties.

In one embodiment, the present invention relates to a method of administering a therapeutic agent to a mammal, comprising:

(i) administering a solution comprising (a) a substituted fullerene, comprising (a-i) a fullerene moiety comprising n carbon atoms, wherein n is an integer and $60 \leq n \leq 240$, and (a-ii) a functional group selected from the group consisting of biotin-containing moieties, antigen-binding moieties, and tissue-recognition moieties, and (b) a pharmaceutically effective amount of the therapeutic agent, wherein the therapeutic agent is associated with the substituted fullerene.

The substituted fullerene and the therapeutic agent are as described above. In one embodiment, the therapeutic agent is an anti-cancer drug.

In one embodiment, the method further comprises (ii) administering an adjuvant to the mammal, wherein the adjuvant facilitates dissociation of the therapeutic agent from the substituted fullerene. An appropriate adjuvant for a particular substituted fullerene and a particular therapeutic agent can be selected in light of the discussion above.

The ability of vesicles, alternatively referred to as liposomes, to function as drug delivery vehicles is well known in the art, as discussed above and as known from work by Alza Corporation (Mountain View, Calif.), the University of California, and Sequus Pharmaceuticals, among other entities.

In another embodiment, the present invention relates to a derivatized carbon nanotube, comprising:

a carbon nanotube, and at least one therapeutic agent, wherein each therapeutic agent is either covalently attached to the carbon nanotube or present within the carbon nanotube.

As is well known, carbon has not only the propensity to self-assemble from a high temperature vapor to form perfect spheroidal closed cages (fullerenes), but also, with the aid of a transition metal catalyst, to assemble into single-wall cylinders with may be sealed at one or both ends with a semifullerene dome. These tubes may be thought of as two-dimensional single crystals of carbon. Multi-wall cylinders, comprising nested single-wall cylinders, have also been observed. Both multi-wall and single-wall cylinders are encompassed by the term "carbon nanotube," as used herein.

In defining carbon nanotubes, it is helpful to use a recognized system of nomenclature. Herein will be used the carbon nanotube nomenclature described by Dresselhaus et al., *Science of Fullerenes and Carbon Nanotubes*, Ch. 19. Single wall tubular fullerenes are distinguished from each other by a double index (n, m), where n and m are integers that describe how to cut a single strip of hexagonal "chicken-wire" graphite such that its edges join seamlessly when the strip is wrapped onto the surface of a cylinder. When n=m, the resultant tube is said to be of the "arm-chair" or (n, n) type, since when the tube is cut perpendicularly to the tube axis, only the sides of the hexagons are exposed and their pattern around the periphery of the tube edge resembles the arm and seat of an arm chair repeated n times. Regardless of tube type, all single-wall nanotubes have extremely high thermal conductivity and tensile strength. Arm-chair tubes also have extremely high electrical conductivity.

Single-wall carbon nanotubes (SWNTs) are much more likely to be free of defects than are multi-wall carbon nanotubes. This is believed to be because multi-wall carbon nanotubes can survive occasional defects, whereas SWNTs have no neighboring walls to compensate for defects by forming bridges between unsaturated carbon valences. Since single-wall carbon nanotubes have fewer defects, they are generally stronger, more conductive, and typically more useful than multi-wall carbon nanotubes of similar diameter. However, both SWNTs and multi-wall carbon nanotubes may be used within the scope of the present invention. The precise structure of an SWNT or a multiwall carbon nanotube is not crucial and is a matter of routine experimentation to one of ordinary skill in the art. SWNTs often have a diameter of about 0.3 nm to about 8 nm. In one embodiment, the SWNT has a diameter of about 1.2 nm. Multi-wall carbon nanotubes often have a diameter of about 30 nm to about 200 nm.

In one embodiment, the carbon nanotube is a single-wall carbon nanotube wherein m+n=2 to 20. In one embodiment, the carbon nanotube is a single-wall nanotube with (10,10) structure.

The at least one therapeutic agent is selected from any therapeutic agent which can be covalently bonded to the carbon nanotube. The term "at least one therapeutic agent" encompasses both one or more molecules of a single therapeutic agent and one or more molecules of each of one or more therapeutic agent. In one embodiment, the therapeutic agent can be bonded to the carbon nanotube through one or more bonds between one or more carbons of the carbon nanotube and one or more atoms of the therapeutic agent. In one embodiment, the one or more atoms of the therapeutic agent are selected from the group consisting of carbon, oxygen, and nitrogen. Preferably, the bonds are single bonds.

In this embodiment, any desirable therapeutic agent can be bonded to the carbon nanotube. In one embodiment, the therapeutic agent is as described above.

In another embodiment, the therapeutic agent can be present within the carbon nanotube. In one embodiment, the therapeutic agent is as described above.

The derivatized carbon nanotube can further comprise other moieties. In one embodiment, the derivatized carbon nanotube further comprises a functional group selected from the group consisting of biotin, biotin-containing moieties, antigen-binding moieties, and tissue-recognition moieties, as described above.

In another embodiment, the present invention relates to a method of delivering a therapeutic agent to a mammal, comprising (i) administering to the mammal a derivatized carbon nanotube, comprising a carbon nanotube and at least one therapeutic agent, wherein each therapeutic agent is covalently attached to the carbon nanotube.

The derivatized carbon nanotube is as described above. In one embodiment, the derivatized carbon nanotube further comprises a functional group selected from the group consisting of biotin, biotin-containing moieties, antigen-binding moieties, and tissue-recognition moieties. Such a functional group will enhance the direction of the derivatized carbon nanotube to a desired tissue of the mammal.

The first administering step can be performed via any appropriate route as described above. Typically, the derivatized carbon nanotube is in an aqueous solution, and the solution can further comprise preservatives, adjuvants, and other compounds known in the art. However, other vehicles for the derivatized carbon nanotube (e.g., apolar solution, solid, etc.) can be used.

In one embodiment, the method further comprises:

(ii) administering to the mammal an adjuvant which promotes disruption of the covalent bond between the carbon nanotube and the at least one therapeutic agent, thereby delivering the at least one therapeutic agent to the tissue.

The second administering step can be performed via any appropriate route as described above. The adjuvant administered in the second administering step can be any compound that promotes disruption of the covalent bond linking the at least one therapeutic agent to the carbon nanotube, or can be any compound that enhances the action of the therapeutic agent in any other way. The adjuvant is typically in an aqueous solution, and the solution can further comprise preservatives and other compounds known in the art.

Figure 8:
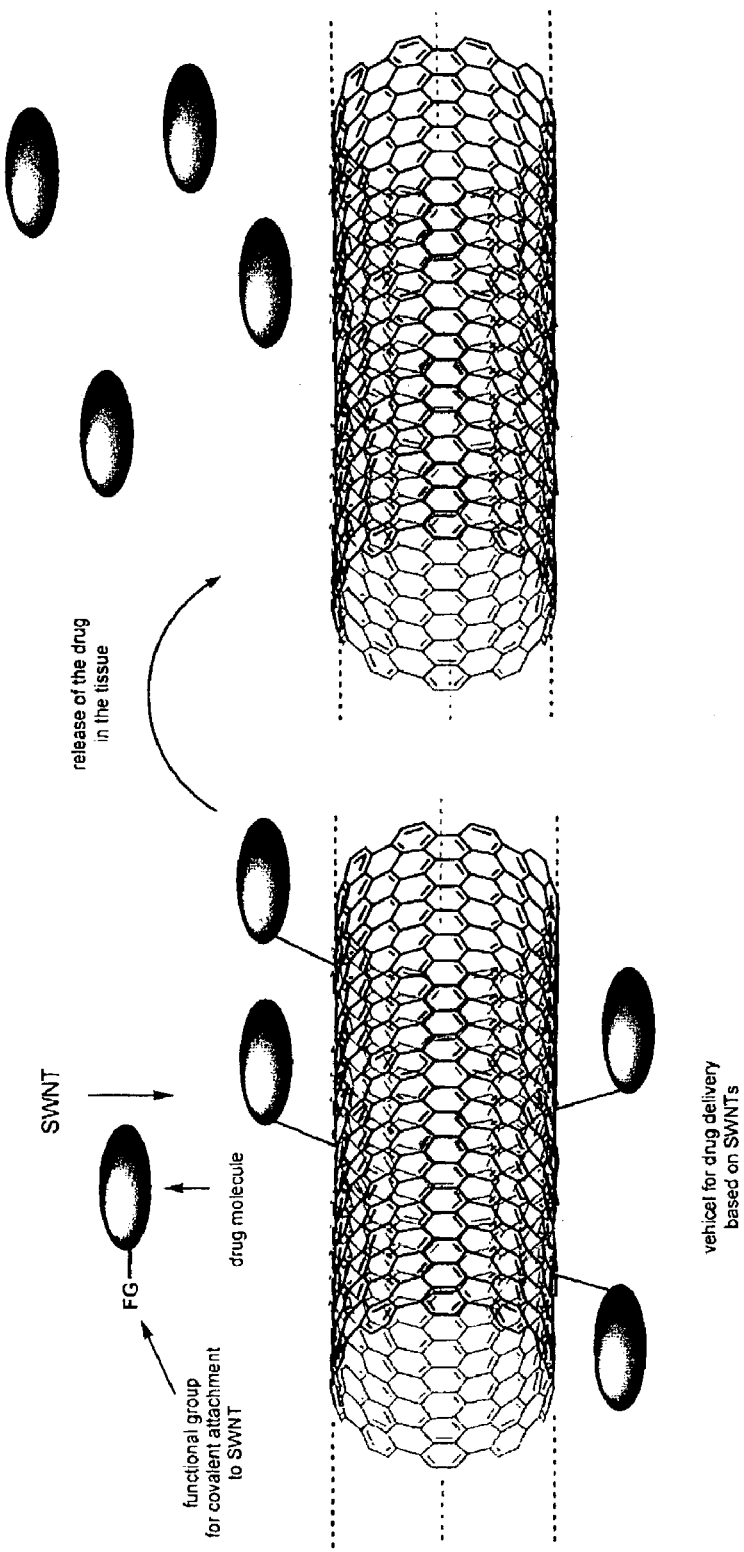
FIG. 8 shows one embodiment of a method of delivering a therapeutic compound by the use of a carbon nanotube.

One embodiment of this method is shown in FIG. 8.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLES

The following examples show that the amphiphilic lipofullerene 1 (Structure III) is able to form stable liposomes (Example 1). The size of the liposomes can be influenced by controlling the pH value of the solution (Example 2). Furthermore, it is possible to functionalize the acid-units of amphiphilic lipofullerenes with a fluorescence-marker or an anchor molecule (Example 3).

Experimental Techniques

Cryo-TEM

A droplet (5 µl) of freshly prepared amphifullerene solution (0.2% (w/v)) in sodium-phosphate buffer (pH=6.84) was placed on a hydrophilized holey carbon filmed grid, was exposed to 60 s plasma treatment at 8 W using a BALTEC MED 020 device, and excess fluid was blotted off to create an ultrathin layer of the solution spanning the holes of the carbon film. The grids were immediately vitrified in liquid ethane at its freezing point (89K) using a standard plunging device. The vitrified samples were transferred under liquid nitrogen into a Philips CM12 transmission electron microscope using the Gatan cryoholder and -stage (Model 626). Microscopy was carried out at −175° C. sample temperature using the microscopes low dose protocol to avoid unnecessary irradiation. The primary magnification was 58,300× and the defocus was chosen to be 0.9 µm, corresponding to a first zero of the CTF (contrast transfer function) at 18 Å (Cs=2 mm).

Dynamic Light Scattering

The amphifullerene was dissolved in dust-free Milli-Q-water and filtered once with either a Millex-GS-Filter (Millipore, pore-size 22 µm) or a Millex-HA-filter (Millipore, pore-size 0.45 µm). All cuvettes and flasks were made dust-free in an acetone fountain. Dynamic lightscattering measurements were carried out with the following apparatus: Stabilite 2060-KR-R krypton ion laser ($\lambda$=647.1 nm) from Spectra-Physics, goniometer SP-86 from ALV, and digital correlator ALV-3000 from ALV.

Monolayer-Experiments

The amphifullerene was dissolved in chloroform at a concentration of 0.2 nmol/µL. For all monolayer experiments at the air/water interface, the subphase contained 0.25 mM EDTA (ethylenediamine tetra-acetic acid) and was buffered with either 25 mM phosphate or 20 mM HEPES (N-2-Hydroxyethylpiperazine-N'-2-ethanesulfonic acid). If not indicated otherwise, the pH was adjusted by NaOH (approximately 13 mM for the phosphate buffer, approximately 4 mM for the HEPES buffer) to pH 7.0. Buffers were prepared using either Millipore purified water. Monolayers of the amphiphilic fullerene-derivative were spread from the organic solution using a microsyringe and afterward compressed to the desired surface pressure.

Film balance experiments at different pH values were carried out on a Langmuir trough with a maximum surface area of 422 cm$^2$ and a subphase temperature of 20.0±0.2° C. for all experiments. The pK-value of the monolayer was determined employing a dedicated film balance equipped with an inner "titration compartment" as follows: A monolayer of the amphifullerene was first compressed to 4.5 mN/m on a subphase of pH 4.0. After this, the channel link between the trough and the titration compartment was pressure tightly closed and the pH of the compartment subphase was successively increased by injecting a total of 500 µL of 1.00 M NaOH into the subphase through the injection hole and the change of $\pi$ was recorded after appropriate equilibration.

Example 1

Formation of a Variety of Stable Aggregates Based on the Amphiphilic Lipofullerene 1 (FIG. 1)

The amphiphilic lipofullerene 1 has the structure shown in FIG. 1. The amphiphilic lipofullerene ("amphifullerene") 1 was observed to spontaneously aggregate in aqueous solution at pH 7.4. The aggregates were stable at least during several days and they did not disaggregate down to a cmc (critical micelle-building constant) of at least 4×10$^{-7}$ mol/L.

Figure 2:
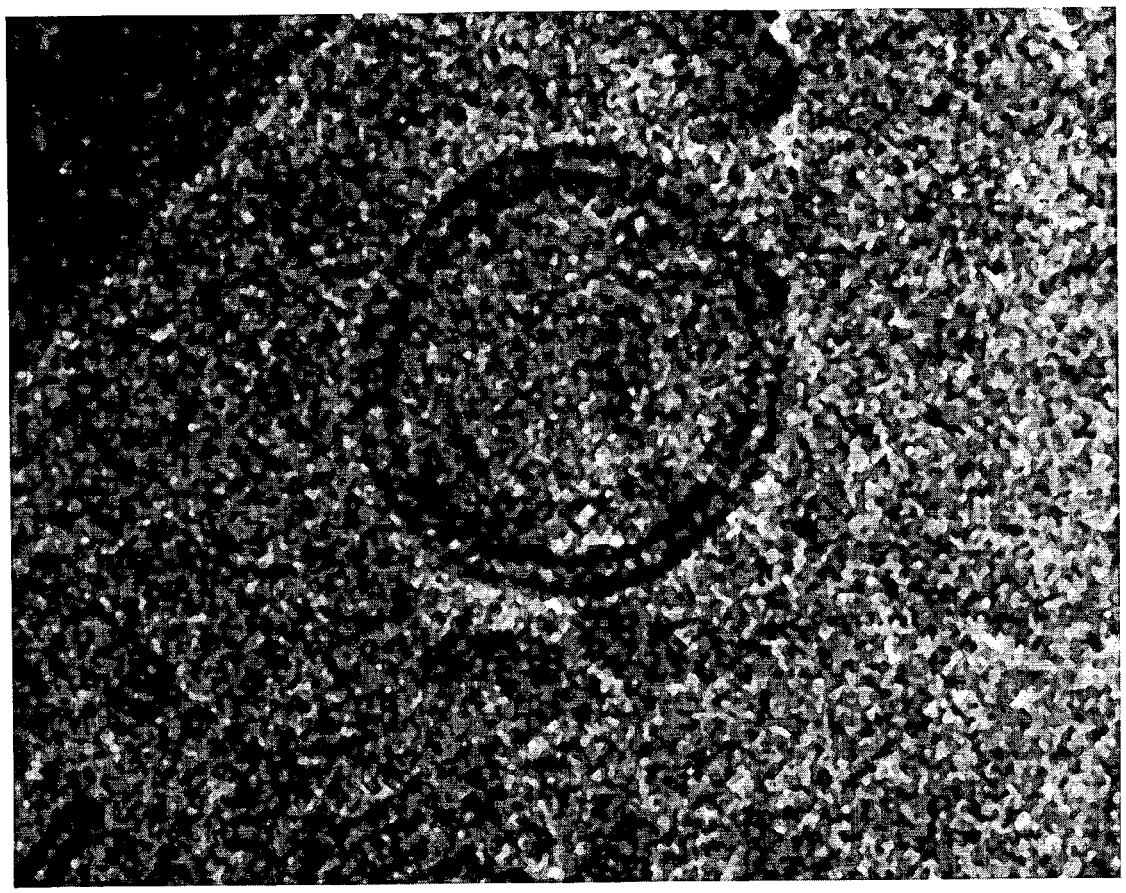
FIG. 2 shows a cryogenic transmission electron microscopy ("cryo-TEM") image of a vesicle comprising the amphifullerene represented by FIG. 1. The vesicle has a diameter of about 80 nm and a thickness of the bilayer of about 7 nm. The dark regions in the bilayer represent the C$_{60}$-core of the amphifullerene.

With light scattering methods and electron microscopy, the size and form of the liposomes were determined. The amphiphilic lipofullerene 1 tended to form unilamellar (bilayer) vesicles and cylindrical micelles. The diameter of these vesicles varied from 50 nm to about 400 nm. The cylindrical micelles had a thickness of 7 nm, which is roughly equivalent to the size of two molecules, and the cylindrical micelles showed different lengths varying from 50 to 200 nm. A cryo-TEM of a typical vesicle is shown in FIG. 2. This vesicle had a diameter of about 80 nm and a thickness of the bilayer of about 7 nm. The dark regions in the bilayer represent the $C_{60}$-core of the amphifullerene.

Example 2

Adjusting the Size of Liposomes by Variation of the pH Value

Due to the $pK_a$ values of the amphifullerene 1, a variation of the degree of protonation is possible and has been observed in a pH range from 6 to 11. Changes in the pH drastically influence the charge density on the surface of liposomes comprising the amphifullerene. Therefore, it was considered possible to change the aggregation properties by differing the pH. This behavior was demonstrated by pH titration experiments on a monolayer of the amphifullerene and by the dependence of light scattering measurements on pH.

Monolayer Experiments

Figure 3:
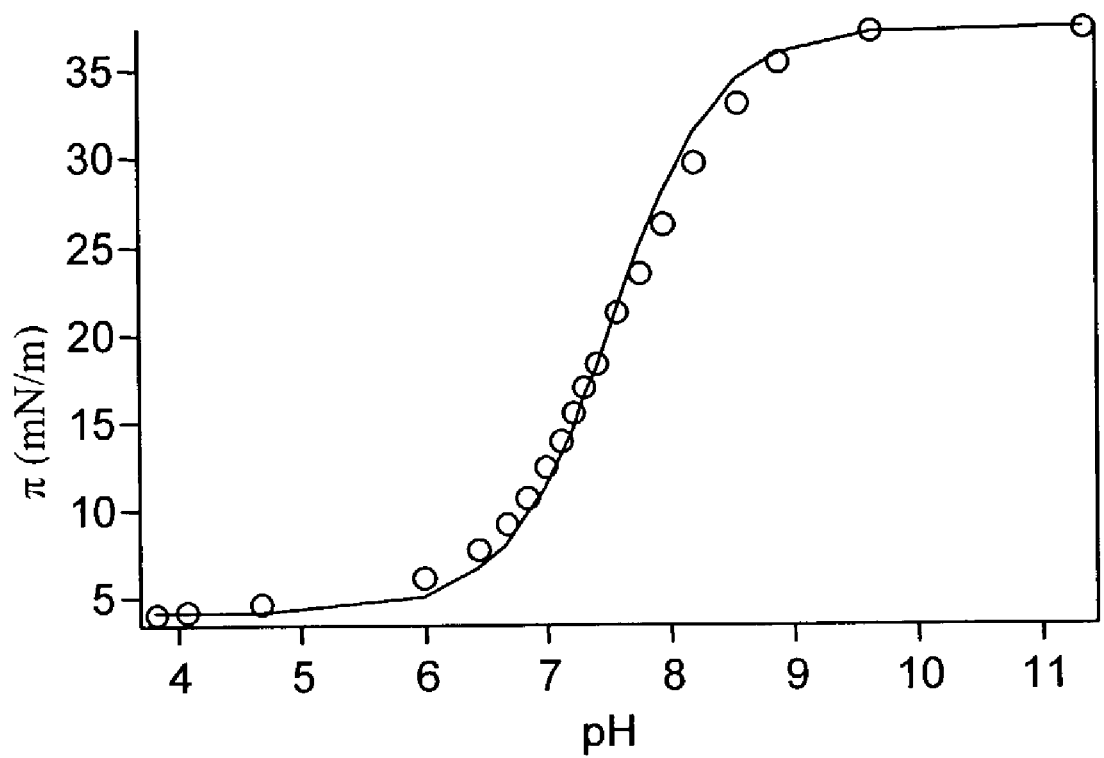
FIG. 3 shows the pressure as a function of a pH for a titration isotherm of a monolayer formed from the amphifullerene represented by FIG. 1.

Even if pH titration of the monolayer does not provide immediate information about the aggregation-behavior in solution, information about the electrostatic interaction at the vesicle surface is readily available. The pressure at the monolayer is directly related to the pH value of the solution and also to the electrostatic interaction between the acid units. With increasing pH, the surface charge increases and with this increase the propensity to form aggregates would be expected to decrease. The dependence of pH on the surface pressure is given in FIG. 3.

Light Scattering Experiments in Solution

The pH-dependent altering of the vesicle size in a solution of liposomes was shown with light-scattering experiments. Table 1 shows that an increase of pH from about 7 to about 11 led to a reduction in the hydrodynamic radius of the vesicle from about 50 nm to about 19 nm. We expect the use of other amphiphilic lipofullerenes would lead to similar adjustments of these values.

TABLE 1

Dependence of vesicle size on pH. ($D_{app}$: apparent diffusion coefficient).

| pH | concentration [g/L] | $D_{app}$ ($q^2 \to 0$) | $R_h$ (hydrodynamic radius) [nm] |
|---|---|---|---|
| 7.2 | 0.6 | 4.30 × 10$^{-8}$ | 49.7 |
| 8.4 | 0.6 | 4.87 × 10$^{-8}$ | 43.9 |
| 11 | 0.6 | 1.14 × 10$^{-7}$ | 18.7 |

Example 3

Functionalization of Amphifullerene 1 with a Fluorescent Molecule or an Anchor Molecule In order to attach biomolecules to amphifullerene 1, we used an anchor molecule. The fluorescence marker Texas Red® (sulforhodamine, commercially available from Molecular Probes, Inc., Eugene, Oreg.) was used in this study.

In another experiment, biotin, which is able to bind to biomolecules (avidin, streptavidin), was attached to amphifullerene 1.

Attachment of Texas Red®

Texas Red® is a fluorophore which is derived from rhodamine and emits at a longer wavelength than other rhodamine derivatives. The preconditions for the labeling were set to 1–2% (maximum of 5%) of labeled amphifullerenes and only one fluorophore moiety per dendrimer as far as possible. The following statistical labeling of the carboxylic end groups was performed in absolute chloroform with freshly prepared standard solutions of carbonyldiimidazole (CDI) in absolute chloroform and of Texas Red® in N,N-dimethylformamide (DMF). The amphifullerene 1 was first partially activated at the carboxylic acid groups by CDI. After 1 hour, 5 mol % of the amino derivative of the fluorophore was added. The coupling was followed by thin layer chromatography (TLC). The solution was stirred for 1 day and subsequently diluted with chloroform and washed with water. The orange-colored chloroform phase was then transferred to a TLC plate and separated by preparative TLC (on a silica TLC plate). After repeated solvation of the amphifullerene-containing fraction with ethanol and precipitation of dissolved silica with methylenechloride, the solution was rotary evaporated and the product was dried in vacuo.

Figure 7:
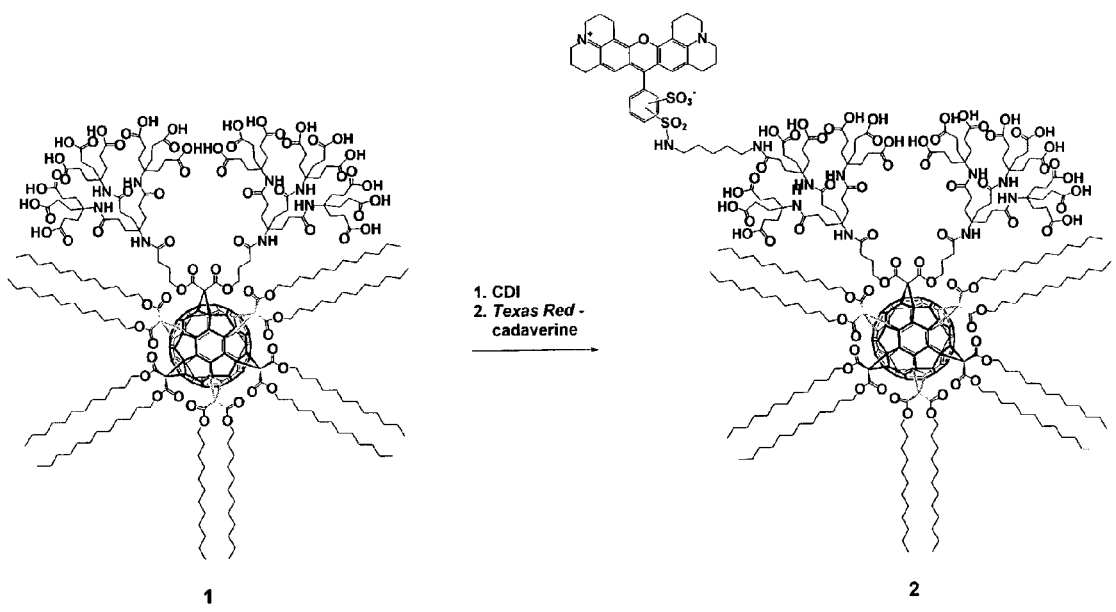
FIG. 7 shows the scheme for synthesis of an amphifullerene labeled with the fluorescence marker Texas Red®. The use of gray follows that of FIG. 1 and FIG. 6.

FIG. 7 shows the synthesis of a dendrofullerene hexakisadduct labeled with the fluorescence marker Texas Red®.

Figure 4:
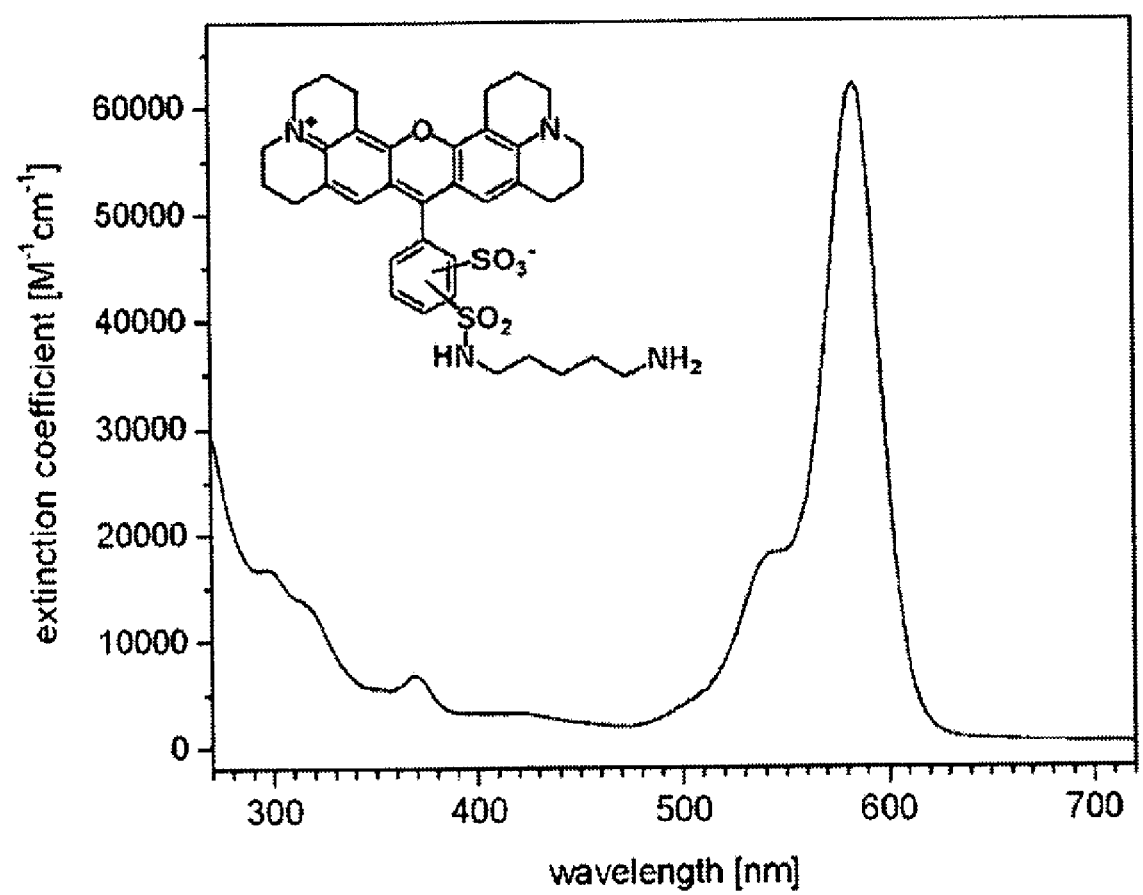
FIG. 4 shows the UV/Vis spectrum of the Texas Red® derivative of the amphifullerene represented by FIG. 1. The Texas Red® derivative is referred to as compound 2 in Scheme 1, Example 3.

The total yield was 78%. Use of a TLC control verified the purity of the product. The ratio of 1 and 2 in the mixture was determined by UV/Vis spectroscopy. The strong absorption band of Texas Red® at 589 nm rendered molecules 2 capable of detection and calibration for the small proportion of fluorophore units (FIG. 4). In literature, an extinction coefficient for Texas Red® in DMF of $81 \times 10^3$ at 591 nm has been reported. Because 4-(dicyanomethylene)-2-methyl-6-(4-dimethylaminostyryl)-4H-pyran (DCM) was used for the characterization of 2, the extinction coefficient for Texas Red® in DCM (presolvated in a small amount of DMF) was determined. The value of 62 ($\pm 0.3$)$\times 10^3$ was obtained.

The extinction coefficients of the amphifullerene 1 in DCM were determined. The values of $\epsilon = 77 \times 10^3$ at 271 nm, $79 \times 10^3$ at 282 nm, $52 \times 10^3$ at 318 nm and $41 \times 10$ nm are in good agreement with the reported values.

Figure 5:
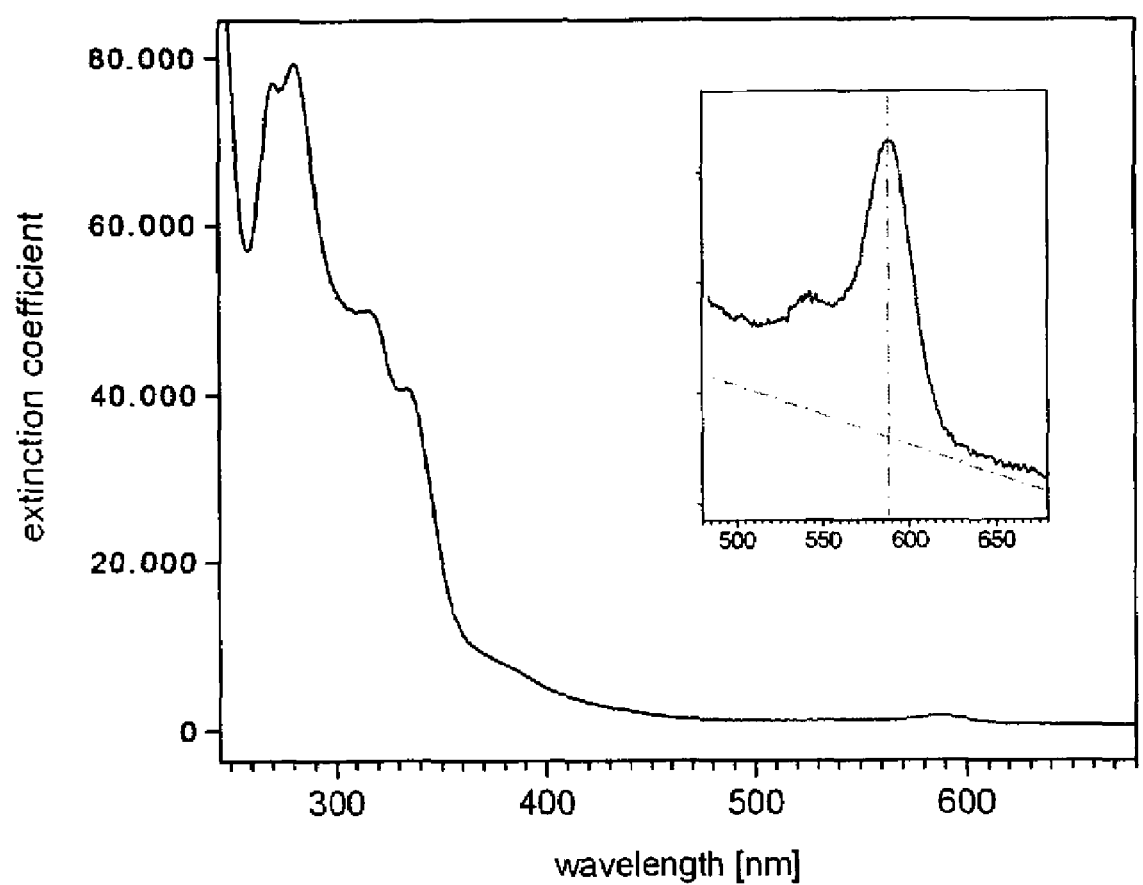
FIG. 5 shows the UV/Vis spectrum of a partially labeled dendrofullerene (compound 2) with 2.0% fluorophore.

The ratio of the extinction coefficients of amphifullerene 1 and fluorophore Texas Red® was used to determine the amount of labeled molecules. With an appropriate baseline correction in the fluorophore region of the UV/Vis spectrum shown in FIG. 5, a labeling ratio of 2.0% was determined.

Attachment of Biotin

Figure 6:
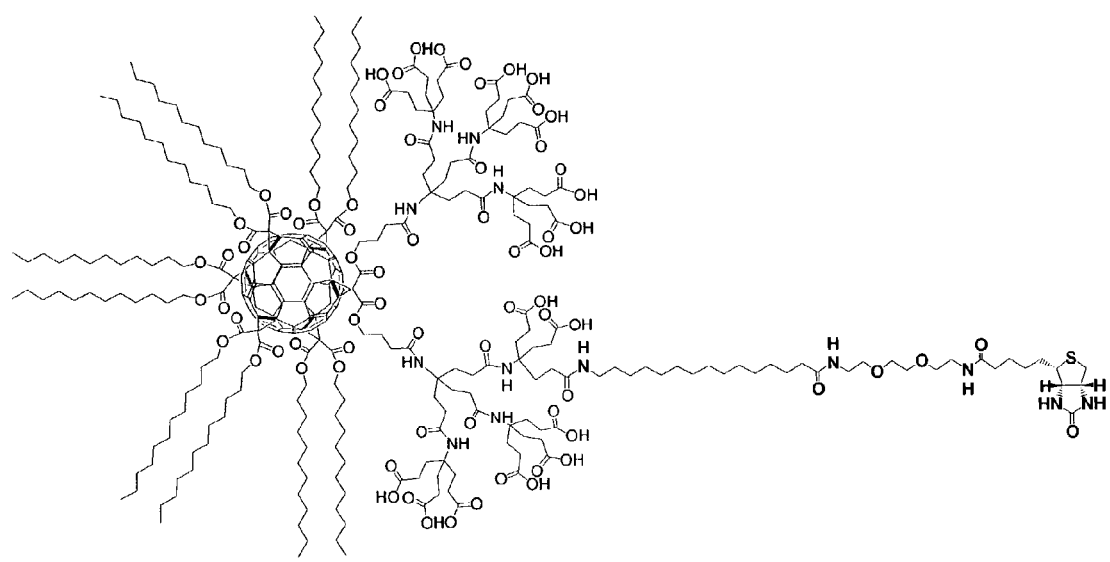
FIG. 6 shows a particular substituted fullerene comprising a functional group, according to the present invention. The use of gray follows that of FIG. 1. The functional group is a biotin-containing moiety and includes a linker moiety.

In a different attempt to functionalize the amphifullerene, the anchor molecule biotin, which is able to bind to biomolecules (avidin, streptavidin), was attached. Based on the coupling-experiments with the fluorophore a biotin-spacer-molecule was attached to the amphifullerene 1 to give the anchor-functionalized amphifullerene 3 (see FIG. 6).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A vesicle having an interior, an exterior, and a wall, wherein the wall comprises one or more layers, wherein each layer comprises a substituted fullerene having structure I:

wherein $C_n$ is a fullerene moiety comprising n carbon atoms, wherein n is an integer and $60 \leq n \leq 240$;

B is an organic moiety comprising from 1 to about 40 polar headgroup moieties;

b is an integer and $1 \leq b \leq 5$;

each B is covalently bonded to the $C_n$ through 1 or 2 carbon-carbon, carbon-oxygen, or carbon-nitrogen bonds;

A is an organic moiety comprising a terminus proximal to the $C_n$ and one or more termini distal to the $C_n$, wherein the termini distal to the $C_n$ each comprise —$C_xH_y$, wherein x is an integer and $8 \leq x \leq 24$, and y is an integer and $1 \leq y \leq 2x+1$;

a is an integer, $1 \leq a \leq 5$;

$2 \leq b+a \leq 6$; and each A is covalently bonded to the $C_n$ through 1 or 2 carbon-carbon, carbon-oxygen, or carbon-nitrogen bonds, wherein the vesicle wall comprises at least about 50 mol % the substituted fullerene; and, wherein the interior of the vesicle, a portion of the wall between two layers, or both comprise a therapeutic agent.

2. The vesicle of claim 1, wherein the wall is a bilayer membrane.

3. The vesicle of claim 1, wherein the wall is a monolayer membrane.

4. The vesicle of claim 1, wherein B comprises 18 polar headgroup moieties; A comprises two termini distal to the $C_n$; x=12; y=25; b=1; and a=5.

5. The vesicle of claim 4, wherein the substituted fullerene molecule has structure II:

wherein X' is >C(C(=O)OC$_3$ H$_6$ C(=O)NHC(C$_2$ H$_4$ C(=O)NHC(C$_2$ H$_4$ C(=O)OH)$_3$)$_3$)$_2$ and each X is >C(C(=O)O(CH$_2$)$_{11}$CH$_3$)$_2$.

6. The vesicle of claim 5, wherein the substituted fullerene molecule has the structure

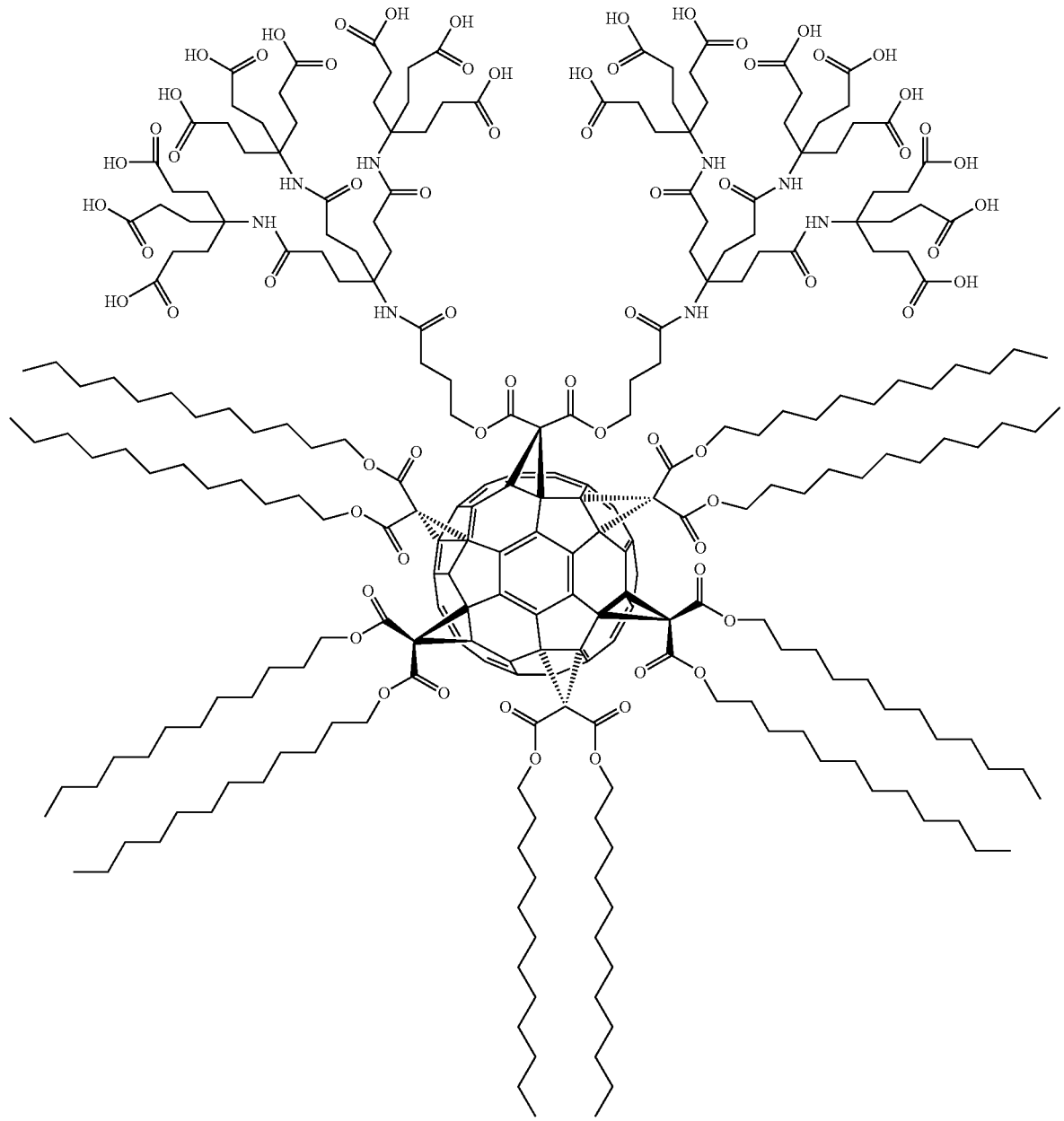

7. The vesicle of claim 1, wherein from about 0.01 mole % to about 100 mole % of the substituted fullerene molecules further comprise a functional group covalently linked to a B group.

8. The vesicle of claim 7, wherein the functional group is selected from the group consisting of biotin-containing moieties, antigen-binding moieties, and tissue-recognition moieties.

9. The vesicle of claim 8, wherein the substituted fullerene comprising the functional group has the structure.

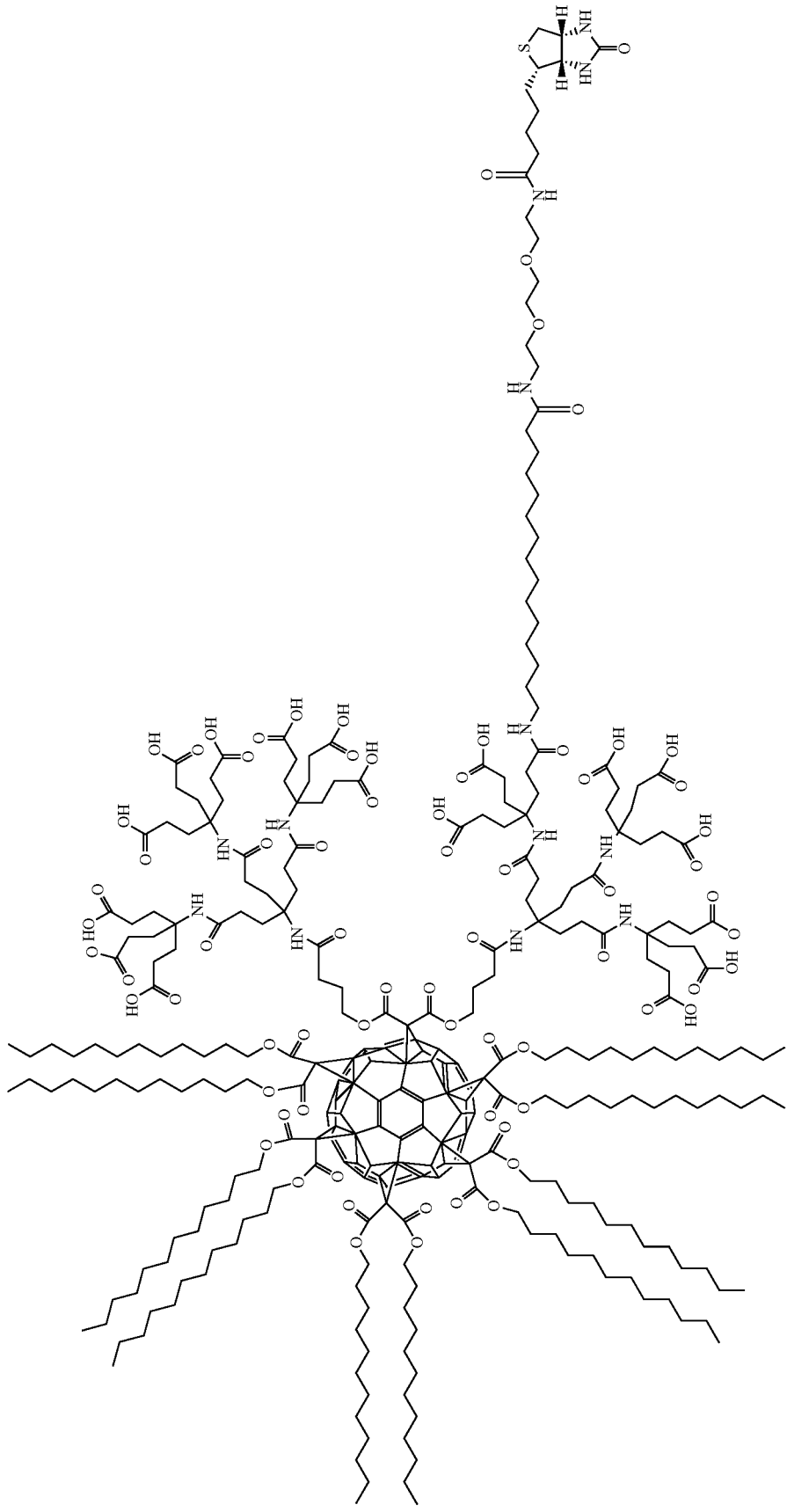

10. The vesicle of claim 1, wherein the wall comprises at least about 75 mol % a substituted fullerene having structure I.

11. The vesicle of claim 1, wherein the therapeutic agent is an anti-cancer drug.

12. A method of administering a therapeutic agent to a mammal, comprising:
(i) administering a solution comprising a pharmaceutically effective amount of the therapeutic agent, wherein the therapeutic agent is present in (a) the interior of a vesicle having an interior, an exterior, and a wall, (b) a portion of the wall between two layers, or (c) both, to the mammal, wherein the wall comprises one or more layers, wherein each layer comprises a substituted fullerene having structure I:

$(B)_b\text{—}C_n\text{-}(A)_a$ (I)

wherein $C_n$ is a fullerene moiety comprising n carbon atoms, wherein n is an integer and $60 \leq n \leq 240$;
B is an organic moiety comprising from 1 to about 40 polar headgroup moieties;
b is an integer and $1 \leq b \leq 5$;
each B is covalently bonded to the $C_n$ through 1 or 2 carbon-carbon, carbon-oxygen, or carbon-nitrogen bonds;
A is an organic moiety comprising a terminus proximal to the $C_n$ and one or more termini distal to the $C_n$, wherein the termini distal to the $C_n$ each comprise —$C_xH_y$, wherein x is an integer and $8 \leq x \leq 24$, and y is an integer and $1 \leq y \leq 2x+1$;
a is an integer, $1 \leq a \leq 5$;
$2 \leq b+a \leq 6$; and
each A is covalently bonded to the $C_n$ through 1 or 2 carbon-carbon, carbon-oxygen, or carbon-nitrogen bonds,
wherein the vesicle wall comprises at least about 50 mol % the substituted fullerene.

13. The method of claim 12, wherein the wall is a bilayer membrane.

14. The method of claim 12, wherein the wall is a monolayer membrane.

15. The method of claim 12, wherein from about 0.01 mole % to about 100 mole % of the substituted fullerene molecules further comprise a functional group covalently linked to a B group.

16. The method of claim 15, wherein the functional group is selected from the group consisting of biotin-containing moieties, antigen-binding moieties, and tissue-recognition moieties.

17. The method of claim 12, wherein the wall comprises at least about 75 mol % a substituted fullerene having structure I.

18. The method of claim 12, wherein the therapeutic agent is an anti-cancer drug.

19. The method of claim 12, further comprising
(ii) administering an adjuvant to the mammal, wherein the adjuvant facilitates recognition of the tissue by a functional group, if any, covalently bonded to the substituted fullerene in the layer of the wall adjacent to the vesicle exterior; union of the vesicle with the membrane of a cell of the tissue; or both.

20. The method of claim 12, further comprising:
(ii) disaggregating the vesicle.

21. A method of reversibly forming a vesicle having an interior, an exterior, and a wall, wherein the wall comprises one or more layers and the interior of the vesicle, a portion of the wall between two layers, or both comprise a therapeutic agent, comprising:
dissolving in an aqueous solvent (a) a substituted fullerene having the structure I:

$(B)_b\text{—}C_n\text{-}(A)_a$ (I)

wherein $C_n$ is a fullerene moiety comprising n carbon atoms, wherein n is an integer and $60 \leq n \leq 240$;
B is an organic moiety comprising from 1 to about 40 polar headgroup moieties;
b is an integer and $1 \leq b \leq 5$;
each B is covalently bonded to the $C_n$ through 1 or 2 carbon-carbon, carbon-oxygen, or carbon-nitrogen bonds;
A is an organic moiety comprising a terminus proximal to the $C_n$ and one or more termini distal to the $C_n$, wherein the termini distal to the $C_n$ each comprise —$C_xH_y$, wherein x is an integer and $8 \leq x \leq 24$, and y is an integer and $1 \leq y \leq 2x+1$;
a is an integer, $1 \leq a \leq 5$;
$2 \leq b+a \leq 6$; and
each A is covalently bonded to the $C_n$ through 1 or 2 carbon-carbon, carbon-oxygen, or carbon-nitrogen bonds, and
(b) the therapeutic agent,
wherein the pH of the solvent is sufficiently low to form a vesicle from the substituted fullerene and the vesicle comprise at least 50 mole % of the fullerene.

22. The method of claim 21, wherein the wall is a bilayer membrane.

23. The method of claim 21, wherein the wall is a monolayer membrane.

24. The method of claim 21, wherein the pH is less than about 8.0.

25. The method of claim 21, further comprising disaggregating the vesicle.

* * * * *

UNITED STATES PATENT AND TRADEMARK OFFICE
CERTIFICATE OF CORRECTION

PATENT NO. : 7,070,810 B2  
APPLICATION NO. : 10/367646  
DATED : July 4, 2006  
INVENTOR(S) : Andreas Hirsch, Uri Sagman and Stephen R. Wilson Page 1 of 1

It is certified that error appears in the above-identified patent and that said Letters Patent is hereby corrected as shown below:

In column 28, claim 21, line 42, delete "comprise" and insert --comprises-- .

Signed and Sealed this

Twenty-second Day of August, 2006

JON W. DUDAS  
*Director of the United States Patent and Trademark Office*